(12) United States Patent
O'Connor et al.

(10) Patent No.: US 10,449,043 B2
(45) Date of Patent: Oct. 22, 2019

(54) DISPLACEMENT BASED LOCK AND RELEASE MECHANISM

(71) Applicant: BOSTON SCIENTIFIC SCIMED, INC., Maple Grove, MN (US)

(72) Inventors: Tim O'Connor, Galway (IE); Richard O'Sullivan, Turloughmore (IE); Art Flannery, Mountain View, CA (US); Takashi H. Ino, San Jose, CA (US); Daniel J. Foster, Lino Lakes, MN (US); James P. Rohl, Prescott, WI (US); Patricia McAfee, Galway (IE); Marc Feeley, Swinford (IE); Sumit Agrawal, Woodbury, MN (US); John Darst, Oakland, MN (US); Noel Boyhan, Castlepollard (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 828 days.

(21) Appl. No.: 14/995,527

(22) Filed: Jan. 14, 2016

(65) Prior Publication Data
US 2016/0206423 A1 Jul. 21, 2016

Related U.S. Application Data

(60) Provisional application No. 62/104,322, filed on Jan. 16, 2015.

(51) Int. Cl.
*A61F 2/24* (2006.01)

(52) U.S. Cl.
CPC ............ *A61F 2/243* (2013.01); *A61F 2/2418* (2013.01); *A61F 2/2436* (2013.01); *A61F 2220/0008* (2013.01); *A61F 2220/0033* (2013.01)

(58) Field of Classification Search
CPC ........ A61F 2/24; A61F 2/2436; A61F 2/2439; A61F 2220/0008; A61F 2220/0033
See application file for complete search history.

(56) References Cited

U.S. PATENT DOCUMENTS

| 15,192 A | 6/1856 | Peale |
| 2,682,057 A | 6/1954 | Lord |
(Continued)

FOREIGN PATENT DOCUMENTS

| CN | 1338951 A | 3/2002 |
| DE | 19532846 A1 | 3/1997 |
(Continued)

OTHER PUBLICATIONS

US 8,062,356 B2, 11/2011, Salahieh et al. (withdrawn)
(Continued)

*Primary Examiner* — Diane D Yabut
(74) *Attorney, Agent, or Firm* — Seager, Tufte & Wickhem LLP

(57) ABSTRACT

A medical device system may include a valve replacement implant including an anchor member reversibly actuatable between a delivery configuration and a deployed configuration, wherein the implant includes at least one locking element configured to lock the anchor member in the deployed configuration, and at least one actuator element configured to engage the at least one locking element and actuate the anchor member between the delivery configuration and the deployed configuration. The at least one actuator element may include a self-biased cam mechanism configured to extend into and engage a first locking portion of the at least one locking element.

14 Claims, 21 Drawing Sheets

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |

(56) References Cited

U.S. PATENT DOCUMENTS

| | | |
|---|---|---|
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Alba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B1 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |

(56) References Cited

U.S. PATENT DOCUMENTS

| | | |
|---|---|---|
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |

(56) References Cited

U.S. PATENT DOCUMENTS

| | | |
|---|---|---|
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |

(56) References Cited

U.S. PATENT DOCUMENTS

| | | |
|---|---|---|
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0049313 A1 | 2/2010 | Alon et al. |
| 2010/0094399 A1 | 4/2010 | Dorn et al. |

(56) References Cited

U.S. PATENT DOCUMENTS

| | | | |
|---|---|---|---|
| 2010/0121434 A1 | 5/2010 | Paul et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | | |
|---|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A2 | 12/2001 |
| WO | 0236048 A2 | 5/2002 |
| WO | 0241789 A2 | 5/2002 |
| WO | 0243620 A1 | 6/2002 |
| WO | 0247575 A2 | 6/2002 |
| WO | 02056955 A2 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A1 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A1 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |

(56) References Cited

FOREIGN PATENT DOCUMENTS

| | | | |
|---|---|---|---|
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, 1992.
Atwood et al., "Insertion of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses." Pergamon Publishing Corporation. New York, 1991: 307-322.
Boudjemline et al., "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcitic Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.

Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759, 2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Moulopoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Paniagua et al., "Heart Watch." Texas Heart Institute. Spring, 2004. Edition: 8 pages.
Pavcnik et al., "Percutaneous Bioprosthetic Veno Valve: A Long-term Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. 9-17, 2004.
Vahanian et al., "Percutaneous Approaches to Valvular Disease." Circulation, 109: 1572-1579, 2004.
Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
Examiner's First Report on AU Patent Application No. 2011202667, dated May 17, 2012.
"A Matter of Size." Treiennial Review of the National Nanotechnology Initiative, The National Academies Press, Wshington DC, v-13, 2006, http://www.nap.edu/catalog/11752/a-matter-of-size-triennial-review-of-the-national-nanotechnology.
Atwood et al., "Insertion of Heart Valves by Catheterization." The Capstone Design Course Report MIME 1501-1502. Technical Design Report Northeastern University, pp. 1-93, Nov. 5, 2007.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report dated Aug. 10, 2011 for EP Application No. 06824992.9.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, 2006.

(56) References Cited

OTHER PUBLICATIONS

Levy, "Mycobacterium Chelonei Infection of Porcine Heart Valves." The New England Journal of Medicine, Washington DC, 297(12), Sep. 22, 1977.
Supplemental Search Report from EP Patent Office, EP Application No. 05758878.2, dated Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano. "Mid-term Results of the Valve-on-Valve Technique for Bioprosthetic Failure." European Journal of Cardiothoracic Surgery: 453-457, 2000.
Topol. "Percutaneous Expandable Prosthetic Valves." Textbook of Interventional Cardiology, W.B. Saunders Company, 2: 1268-1276, 1994.
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Bodnar et al., "Replacement Cardiac Valves R Chapter 13: Extinct Cardiac Valve Prostheses." Pergamon Publishing Corporation. New York, 307-322, 1991.
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May, 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Percutaneous Heart Valve in the Chronic in Vitro Testing Model." Circulation, 106: e51-e52, Sep. 17, 2002.
Paniagua et al., "Heart Watch." Texas Heart Institute. Edition: 8 pages, Spring, 2004.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. Feb. 9-17, 2004.
Stassano. "Mid-term Results of the Valve-on-Valve Technique for Bioprosthetic Failure." European Journal of Cardiothoracic Surgery: vol. 18, 453-457, Oct. 2000.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
Cunanan et al., "Tissue Characterization and Calcification Potential of Commercial Bioprosthetic Heart Valves." Ann. Thorac. Surg., S417-421, May 15, 2001.
Laborde et al., "Percutaneous Implantation of the Corevalve Aortic Valve Prosthesis for Patients Presenting High Risk for Surgical Valve Replacement." EuroIntervention: 472-474, Feb. 2006.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.

DISPLACEMENT BASED LOCK AND RELEASE MECHANISM

RELATED APPLICATIONS

This application claims priority to U.S. Provisional Application Ser. No. 62/104,322, filed Jan. 16, 2015.

TECHNICAL FIELD

The present disclosure pertains to medical devices, and methods for manufacturing and/or using medical devices. More particularly, the present disclosure pertains to locking mechanisms for a medical device and/or a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical device system may comprise a valve replacement implant including an anchor member reversibly actuatable between a delivery configuration and a deployed configuration, wherein the implant includes at least one locking element configured to lock the anchor member in the deployed configuration, and at least one actuator element configured to engage the at least one locking element and actuate the anchor member between the delivery configuration and the deployed configuration. The at least one actuator element may include a self-biased cam mechanism configured to extend into and engage a first locking portion of the at least one locking element.

In addition or alternatively, and in a second aspect, the first locking portion includes a longitudinally-oriented passageway extending therethrough, and at least one side aperture extending transversely through a side wall of the first locking portion to the passageway, the at least one side aperture being configured to receive the cam mechanism therein such that the cam mechanism extends through the at least one side aperture.

In addition or alternatively, and in a third aspect, the first locking portion of the at least one locking element is fixedly attached to the anchor member and a second locking portion of the at least one locking element is fixedly attached to the anchor member, the first locking portion and the second locking portion being longitudinally movable relative to each other in the delivery configuration.

In addition or alternatively, and in a fourth aspect, the first locking portion is fixedly attached to a distal portion of the anchor member and the second locking portion is fixedly attached to a proximal portion of the anchor member.

In addition or alternatively, and in a fifth aspect, the second locking portion includes a base portion having a longitudinal axis extending between a proximal end and a distal end, the base portion defining a top surface and a bottom surface, a body portion defining a longitudinal channel extending therethrough, at least a part of the body portion extending upwardly from the base portion, and a flap portion extending toward the proximal end from the body portion. The base portion may include a plurality of protrusions extending upwardly from the top surface proximal of the flap portion. The second locking portion may be configured to slidably receive the first locking portion within the longitudinal channel.

In addition or alternatively, and in a sixth aspect, the body portion may include at least one ramp tapering into the longitudinal channel at the distal end thereof. The at least one ramp may be configured to engage the cam mechanism and urge the cam mechanism extending through the at least one side aperture inwardly, thereby releasing the at least one actuator element from the first locking portion.

In addition or alternatively, and in a seventh aspect, the flap portion includes a second transversely-oriented ridge extending downwardly toward the base portion and laterally across the base portion, such that when the second locking portion is viewed along the longitudinal axis, the second transversely-oriented ridge obstructs at least a portion of the longitudinal channel.

In addition or alternatively, and in an eighth aspect, the plurality of protrusions extends upwardly to a height above the top surface greater than a proximalmost edge of the flap portion.

In addition or alternatively, and in a ninth aspect, the plurality of protrusions extends laterally to a distance from the longitudinal axis equal to or greater than the flap portion.

In addition or alternatively, and in a tenth aspect, the flap portion is self-biased toward an equilibrium position relative to the base portion.

In addition or alternatively, and in an eleventh aspect, the first locking portion includes an engagement portion having a first transversely-oriented ridge adjacent a proximal end thereof.

In addition or alternatively, and in a twelfth aspect, the flap portion engages the first transversely-oriented ridge in the deployed configuration.

In addition or alternatively, and in a thirteenth aspect, the cam mechanism includes a first leg having a transversely extending first projection configured to engage the first locking portion.

In addition or alternatively, and in a fourteenth aspect, the cam mechanism may include a second leg having a transversely extending second projection, the second projection extending in a direction opposite the first projection.

In addition or alternatively, and in a fifteenth aspect, the at least one actuator element includes a retractable release pin disposed alongside the first leg, thereby preventing the cam mechanism from disengaging the first locking portion.

In addition or alternatively, and in a sixteenth aspect, the retractable release pin is slidably disposed within a bore of the at least one actuator element.

In addition or alternatively, and in a seventeenth aspect, a profile of the second locking portion includes a generally rectangular pocket between the flap portion and the top surface, and a passageway extending proximally from the pocket in a curve extending toward the bottom surface around a proximalmost tip of the flap portion and then back away from the bottom surface between the proximalmost tip of the flap portion and the plurality of protrusions to an upwardly-facing opening. The plurality of protrusions may define an upwardmost edge disposed at a greater distance from the bottom surface than a bottommost edge of the flap portion.

In addition or alternatively, and in an eighteenth aspect, a method of releasing a heart valve replacement implant from a delivery device, wherein the implant includes an anchor member reversibly actuatable between a delivery configuration and a deployed configuration and at least one locking element configured to lock the anchor member in the deployed configuration, and the delivery device includes at least one actuator element configured to engage the at least one locking element and actuate the anchor member between the delivery configuration and the deployed configuration, wherein the at least one actuator element includes a self-biased cam mechanism configured to extend into and engage a first locking portion of the at least one locking element, the method comprising: guiding the implant to a target location in the delivery configuration with the delivery device; retracting the at least one actuator element such that a first transverse ridge on the first locking portion engages a second transverse ridge on a second locking portion, thereby locking the anchor member in the deployed configuration; receiving tactile feedback that the anchor member has achieved the deployed configuration; further retracting the at least one actuator element to disengage the at least one actuator element from the first locking portion; and withdrawing the at least one actuator element from the at least one locking element, thereby leaving the implant at the target location.

In addition or alternatively, and in a nineteenth aspect, the tactile feedback includes an increase in force required to retract the at least one actuator element.

In addition or alternatively, and in a twentieth aspect, a method of releasing a heart valve replacement implant from a delivery device may include the steps of: after receiving tactile feedback, verifying positioning of the implant within the target location; advancing the at least one actuator element distally to unlock the anchor member from the deployed configuration; repositioning the implant at the target location; and retracting the at least one actuator element to re-lock the anchor member in the deployed configuration.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
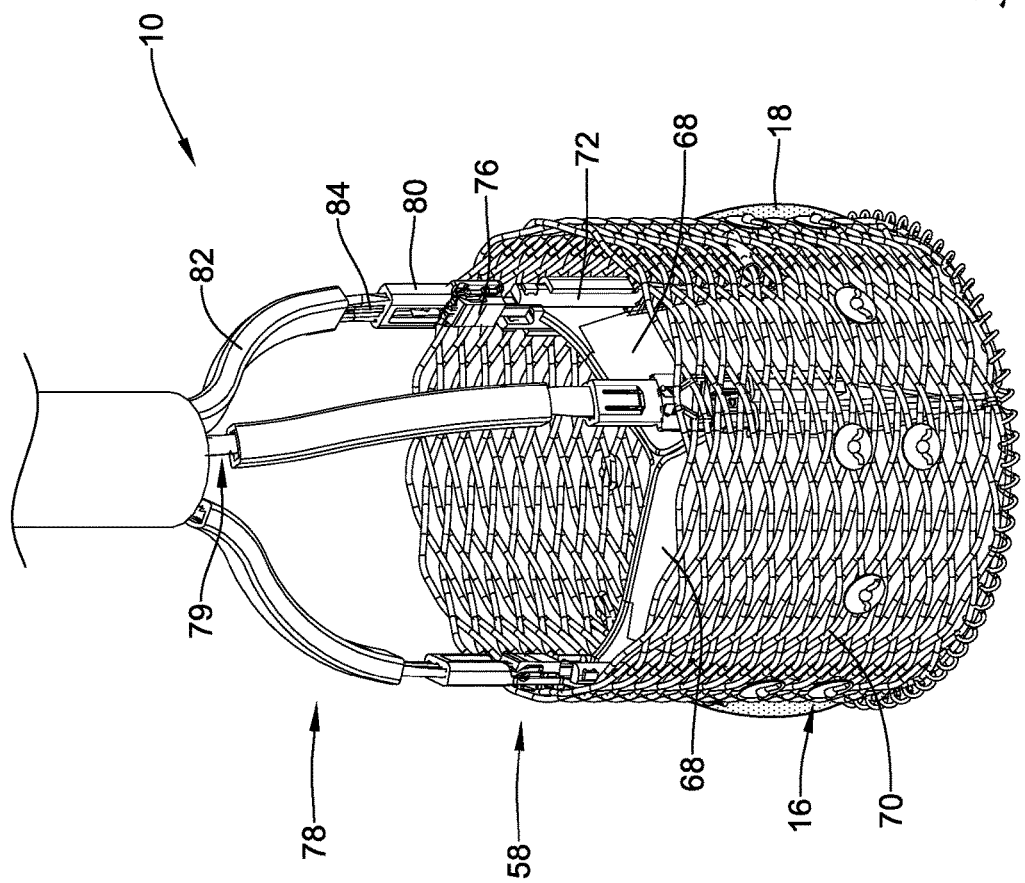
FIG. 1 is a perspective view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Generally speaking, in terms of the orientation of the structural elements relative to each other and the operation of the disclosed device(s), a proximal end may be considered closest to the user (or external to a patient) and a distal end farthest from the user (or internal to a patient). However, the skilled artisan will appreciate that the orientations and/or directions may be reversed as necessary or appropriate.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10 may generally be described as a catheter system that may include a catheter or an outer sheath and a tube or an inner catheter extending at least partially through the outer sheath. A medical implant 16 (i.e., a valve replacement implant, for example) may be coupled to the inner catheter and disposed within a lumen of the outer sheath during delivery of the medical implant 16. In some embodiments, a handle may be disposed at a proximal end of the outer sheath and/or the inner catheter. In general, the handle may be configured to manipulate the position of the outer sheath relative to the inner catheter, as well as aid in the deployment of the medical implant 16.

In use, the medical device system 10 may be advanced percutaneously through the vasculature to a position adjacent to an area of interest or a target location. For example, the medical device system 10 may be advanced through the vasculature to a position adjacent to a defective aortic valve. During delivery, the medical implant 16 may be generally disposed in an elongated and low profile "delivery" configuration within the outer sheath. Once positioned, the outer sheath may be retracted to expose the medical implant 16. The medical implant 16 may be actuated in order to radially expand the medical implant 16 into a generally shortened and larger profile "deployed" configuration suitable for implantation within the anatomy (as shown in FIG. 1, for example). When the medical implant 16 is suitably deployed within the anatomy, the medical device system 10 can be removed from the vasculature, leaving the medical implant 16 in place in a "released" configuration to function as, for example, a suitable replacement for the native aortic valve. In at least some interventions, the medical implant 16 may be deployed within the native valve (e.g., the native valve is left in place and not excised). Alternatively, the native valve may be removed and the medical implant 16 may be deployed in its place as a replacement.

In some embodiments, the outer sheath may have a proximal portion and a distal portion. In some embodiments, the distal portion may have a slightly enlarged or flared inner diameter, which may provide additional space for holding the medical implant 16 therein. For example, in some embodiments, an inner diameter of outer sheath along a proximal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388 ±0.0508 cm (0.222 ±0.002 inches). In some embodiments, an inner diameter of outer sheath 12 along a distal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). At the distal end of the distal portion may be a distal tip, which in some embodiments may be flared or otherwise have a funnel-like shape. A funnel-like shape may increase the outer diameter (and inner diameter) of the outer sheath at the distal tip and may aid in the sheathing and/or re-sheathing of the medical implant 16 into the outer sheath. For example, in some embodiments, the outer sheath may have an outer diameter in a range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including, but not limited to, children) and/or arrangements for the outer diameter and/or inner diameter of the outer sheath. These contemplated embodiments include outer sheaths with flared or otherwise variable outer diameters, embodiments with constant inner diameters, combinations thereof, and the like. The outer sheath may also have a length that is appropriate for reaching the intended area of interest or the target location within the anatomy. For example, the outer sheath may have a length in the range of about 30 to 200 cm, or about 60 to 150 cm, or about 100 to 120 cm, or about 108 ±0.20 cm. In some embodiments, some, all, or a portion of the outer sheath may also be curved. For example, in some embodiments, a distal section of outer sheath may be curved. In one example, a radius of the curve (measured from the center of outer sheath) may be in the range of about 2 to 6 cm (20 to 60 mm), or about 3 to 4 cm (30 to 40 mm), or about 3.675 cm (36.75 mm). Again, these dimensions are examples and are not intended to be limiting.

It is to be noted that in order to facilitate understanding, certain features of the disclosure may be described in the singular, even though those features may be plural or recurring within the disclosed embodiment(s). Each instance of the features may include and/or be encompassed by the singular disclosure(s). For example, a reference to "the actuator element" may be equally referred to all instances and quantities beyond one of "the at least one actuator element".

FIG. 1 illustrates some selected components of the medical device system 10 and/or the medical implant 16. For example, here it can be seen that the medical implant 16 may include a plurality of valve leaflets 68 (e.g., bovine pericardial) which may be secured to a tubular or cylindrical anchor member or braid 70 that is reversibly actuatable between a "delivery" configuration and a "deployed" configuration. In some embodiments, the medical implant 16 may include at least one locking element 58 configured to lock the anchor member or braid 70 in the "deployed" configuration. In some embodiments, at least one actuator element 84 may be configured to engage the at least one locking element 58 and actuate the anchor member or braid 70 between the "delivery" configuration and the "deployed" configuration. In some embodiments, one actuator element 84 may correspond to, engage with, and/or actuate one locking element 58. In some embodiments, one actuator element 84 may correspond to, engage with, and/or actuate more than one locking element 58. Other configurations are also contemplated.

In some embodiments, the at least one locking element 58 may each comprise a first locking portion 96 (e.g., a T-bar, or other elongate element), for example at the commissure portions of the valve leaflets 68 (first locking portion 96 may sometimes be referred to as a portion of a commissure post 72, which may serve to secure the valve leaflets 68, or the first locking portion 96 may be connected and/or attached to a commissure post 72), and a second locking portion 76 (e.g., a buckle or other receiving element). In other words, in at least some embodiments, a medical implant 16 may include at least one or a plurality of first locking portions 96 and a corresponding at least one or a plurality of second locking portions 76. Other configurations and correspondences are also contemplated. In at least some embodiments, the first locking portion 96 may engage the second locking portion 76 in the "deployed" configuration.

In some embodiments, the first locking portion 96 may include an elongated member having a longitudinally-extending passageway 64 extending therethrough and at least one side aperture 98 extending transversely through a side wall of the first locking portion 96 to the passageway 64 adjacent a distal end of the first locking portion 96, as seen in FIGS. 6-17, for example. In some embodiments, the first locking portion 96 may include one or more laterally-extending bars at a distal end thereof, the one or more laterally-extending bars configured to engage with a proximal end of the commissure post(s) 72, thereby preventing relative movement therebetween. In at least some embodiments, the one or more laterally-extending bars may be distal of the at least one side aperture 98. In some embodiments, the at least one side aperture 98 may include two side apertures 98 positioned on opposing sides of the elongated member and/or the passageway 64, as seen in FIG. 12-17, for example. In some embodiments, the at least one actuator element 84 may be slidably disposed within the passageway 64 and be releasably coupled to the first locking portion 96 by a cam mechanism 86 at or adjacent a distal end of actuator element 84, the cam mechanism 86 extending into and engaging the first locking portion 96 of the at least one locking element 58. In some embodiments, the at least one side aperture 98 may be configured to receive the cam mechanism 86 therein such that the cam mechanism 86 extends through the at least one side aperture 98. In some embodiments, the commissure post 72 and/or the first locking portion 96 may include one or more holes or other features provided to aid in attaching the commissure post 72 and/or the first locking portion 96 to the anchor member or braid 70.

In some embodiments, the first locking portion 96 may include an engagement portion 94 having a first transversely-oriented ridge 100 at or adjacent to a proximal end thereof, the first transversely-oriented ridge 100 being configured to engage with a second transversely-oriented ridge 36 of a flap portion 30 of the second locking portion 76 to axially "lock" the medical implant 16 into the "deployed" configuration. After locking the medical implant 16 into the "deployed" configuration, further proximal retraction of the at least one actuator element 84 may disengage the at least one actuator element 84 from the first locking portion 96, as will be described in more detail below, thereby permitting the withdrawal of the at least one actuator element 84 from the at least one locking element 58 and leaving the medical implant 16 at the target site in a "released" configuration.

In some embodiments, the at least one actuator element 84 may include an unlocking member 102 configured to disengage the first locking portion 96 from the second locking portion 76 upon distal movement of the at least one actuator element 84 after achieving the "deployed" configuration, thereby unlocking the anchor member or braid 70 from the "deployed" configuration. In at least some embodiments, the unlocking member 102 may include a longitudinally-oriented ridge configured to slidably engage the flap portion 30 of the second locking portion 76, thereby raising and/or deflecting the flap portion 30 away from the engagement portion 94 until the second transversely-oriented ridge 36 of the flap portion 30 clears and/or disengages from the first transversely-oriented ridge 100. Further distal translation of the at least one actuator element 84 actuates the medical implant 16 back toward the "delivery" configuration.

In some embodiments, the first locking portion 96 may be secured and/or fixedly attached to the anchor member or braid 70. Other embodiments are contemplated where the first locking portion 96 may be movably or removably attached to the anchor member or braid 70. In some embodiments, the first locking portion 96 may be attached to the anchor member or braid 70 by a suture or tether, or a plurality thereof. In some embodiments, the second locking portion 76 may be secured and/or fixedly attached to the anchor member or braid 70. Other embodiments are contemplated where the second locking portion 76 may be movably or removably attached to the anchor member or braid 70. In some embodiments, the first locking portion 96 may be fixedly attached to the anchor member or braid 70 and the second locking portion 76 may be fixedly attached to the anchor member or braid 70. In some embodiments, one of the first locking portion 96 and the second locking portion 76 may be fixedly attached to the anchor member or braid 70 and the other may be movably or removably attached to the anchor member or braid 70. In some embodiments, the first locking portion 96 may be movably or removably attached to the anchor member or braid 70 and the second locking portion 76 may be movably or removably attached to the anchor member or braid 70. In some embodiments, the first locking portion 96 may be attached (i.e., fixedly attached, movably attached, removably attached, etc.) to a distal portion of the anchor member or braid 70. In some embodiments, the second locking portion 76 may be attached (i.e., fixedly attached, movably attached, removably attached, etc.) to a proximal portion of the anchor member or braid 70.

In some embodiments, the medical implant 16 may include three individual valve leaflets 68 secured to the anchor member or braid 70 at, adjacent to, and/or using (at least in part) three individual, corresponding commissure posts 72. In some embodiments, the valve leaflets 68 may also be secured to a base or "distal end" of the anchor member or braid 70. The first locking portions 96 and/or the commissure posts 72, in turn, may be secured and/or fixedly attached to the anchor member or braid 70 (e.g., along the interior of the anchor member or braid 70) with sutures, adhesives, or other suitable mechanisms. Positioned adjacent to (e.g., aligned with) the plurality of first locking portions 96 are a corresponding plurality of second locking portions 76, which may also be secured and/or fixedly attached to the anchor member or braid 70 (e.g., along the interior of the anchor member or braid 70) with sutures, adhesives, or other suitable mechanisms. In this example, one second locking portion 76 is attached to the anchor member or braid 70 adjacent to each of the three first locking portions 96. Accordingly, the anchor member or braid 70 has a total of three second locking portions 76 and three first locking portions 96 attached thereto. Similarly, one actuator element 84 may be associated with each first locking portion 96 and second locking portion 76, for a total of three actuator elements 84 in the illustrated example(s). Other embodiments are contemplated where fewer or more second locking portions 76, first locking portions 96, and actuator elements 84 may be utilized. In some embodiments, a seal 18 (shown in partial cross-section in FIG. 1) may be disposed about the anchor member or braid 70 and may help to seal the medical implant 16 within a target implant site or area of interest upon deployment.

In some embodiments, attachment between the medical implant 16 and the inner catheter (and/or the outer sheath) may be effected through the use of a coupler 78. The coupler 78 may generally include a cylindrical base (not shown) that may be disposed about and/or attached to the inner catheter. Projecting distally from the base is a plurality of fingers 79 (e.g., two, three, four, etc.) that are each configured to engage with the medical implant 16 at one of the second locking portions 76. In some embodiments, each finger 79 may include two elongated tines 104 (as described further below) held in engagement with one second locking portion 76 by a collar 80 slidably disposed about the finger 79. A guide 82 may be disposed over each of the fingers 79 and may serve to keep the fingers 79 of the coupler 78 associated with the actuator elements 84 extending adjacent to (and axially slidable relative to) the fingers 79 of the coupler 78.

During delivery, the medical implant 16 may be secured at the distal end of the inner catheter by virtue of the two elongated tines 104 of the fingers 79 of the coupler 78 being matingly coupled with a corresponding rail 108 disposed at a proximal end of the second locking portion 76 by the collar 80, and by virtue of the actuator elements 84 being coupled to the corresponding first locking portion 96, as will be explained further below. When the medical implant 16 is advanced within the anatomy to the desired location, the outer sheath may be withdrawn (e.g., moved proximally relative to the inner catheter) to expose the medical implant 16. Then, the actuator elements 84 can be used (e.g., proximally retracted) to axially shorten and/or radially expand and "lock" the medical implant 16 and/or the anchor member or braid 70 from the "delivery" configuration to an expanded or "deployed" configuration by proximally retracting the actuator elements 84 to pull the first locking portions 96 into engagement with the second locking portions 76. Finally, uncoupling the actuator elements 84 from the first locking portions 96, which allows the actuator elements 84 to be pulled proximally through the second locking portions 76, where the unlocking member 102 engages the collar 80 and thereby retracts the collar 80 from the two elongated tines 104. Once the collar 80 has been retracted and the two elongated tines 104 decoupled from the rail 108, the fingers 79 of the coupler 78 may be withdrawn from the medical implant 16 thereby deploying the medical implant 16 (and/or the anchor member or braid 70) in the anatomy in a "released" configuration. In other words, one difference between the "deployed" configuration and the "released" configuration is whether or not the actuator elements 84 are attached to and/or engaged with the locking elements 58 and/or the first locking portions 96. In the "deployed" configuration, the actuator elements 84 are still attached to the locking elements 58 and/or the first locking portions 96, which thus permits the medical implant 16 (and/or the anchor member or braid 70) to be unlocked via distal advancement of the actuator elements 84, as described further below, in order to reposition the medical implant 16, for example.

FIGS. 2-5 illustrate selected components of an example locking element 58 configured to reversibly lock the medical implant 16 (and/or the anchor member or braid 70) in the "deployed" configuration, and the general operation of those components. For simplicity and clarity purposes, only one of the fingers 79, only one of the actuator elements 84, only one of the first locking portions 96, and only one of the second locking portions 76 are shown and discussed (the whole medical implant 16 and/or the anchor member or braid 70 is not shown to facilitate understanding of the locking element(s) 58). However, it will be understood that the following discussion may apply equally to any and/or all of the components for which there are more than one within the medical implant 16 (i.e., the actuator elements 84, the second locking portions 76, the first locking portions 96, etc.) and/or the medical device system 10.

As seen in FIGS. 2-5, each actuator element 84 extends through a guide 82 adjacent to and encompassing the finger 79 of the coupler 78, through the collar 80, through a second locking portion 76, and into a passageway 64 extending longitudinally through a first locking portion 96. The actuator element 84 may be axially translatable through the collar 80 and/or the second locking portion 76. The actuator element 84 may be axially translatable through the first locking portion 96 under certain conditions, as will be explained below. In some embodiments, a distal end of the actuator element 84 may include a self-biased cam mechanism 86 (not visible in FIGS. 2-5) configured to engage and/or extend into at least one side aperture 98 extending transversely through a side wall of the first locking portion 96 to the passageway 64.

Figure 2:
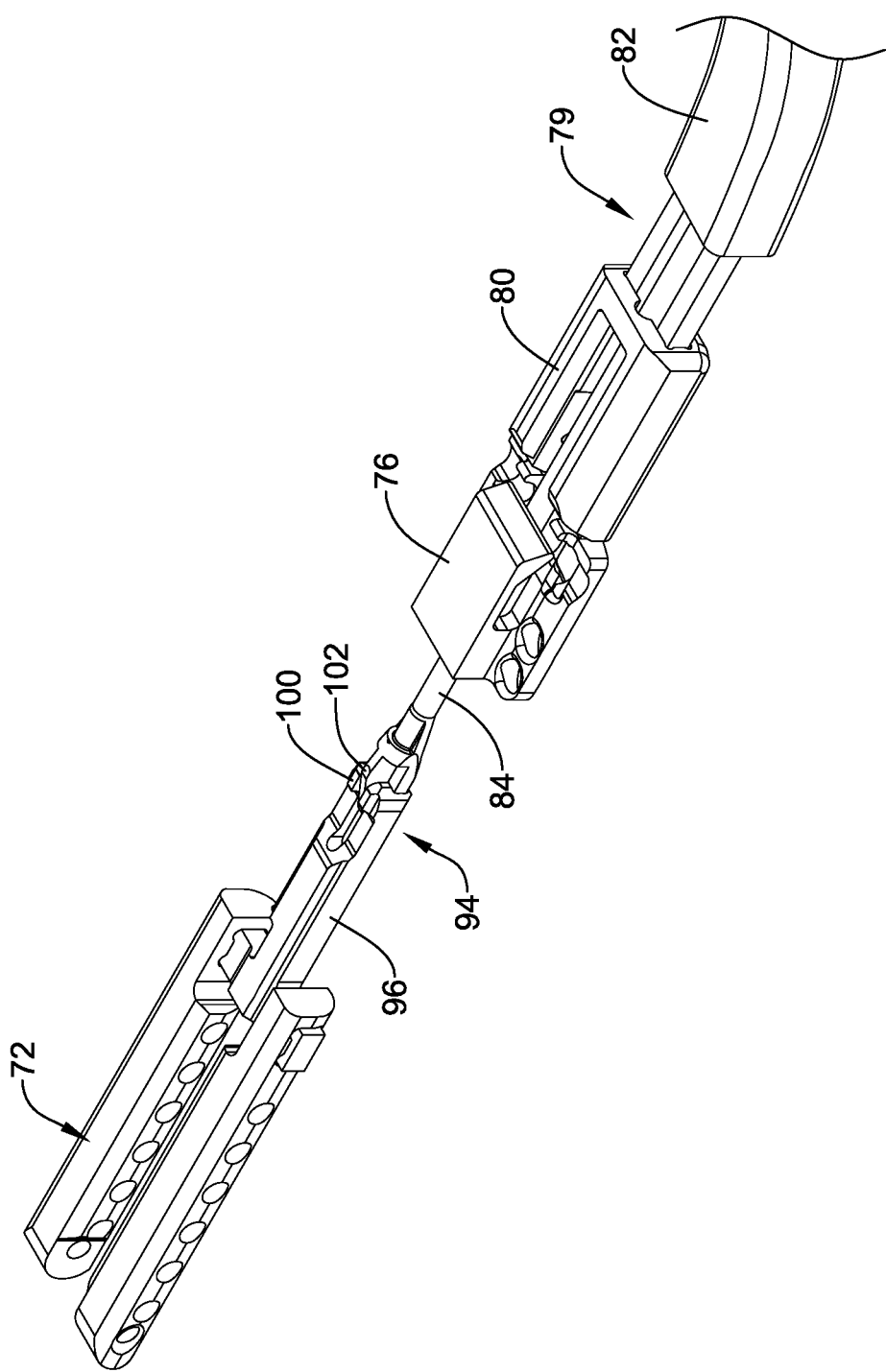
FIG. 2 illustrates selected components of an example implant associated with an example medical device system in a delivery configuration.

The cam mechanism 86 may releasably couple the actuator element 84 to the first locking portion 96 and form a configuration of these structures that can be utilized during delivery of the medical implant 16. As can be appreciated, a proximal end of the first locking portion 96 and a distal end of the second locking portion 76 may be longitudinally separated (as seen in FIG. 2, for example) and, accordingly, the medical implant 16 is in an elongated and generally low-profile "delivery" configuration suitable for percutaneous translation through a patient's anatomy to an area of interest and/or target site. In at least some embodiments, the first locking portion 96 and the second locking portion 76 may be longitudinally moveable and/or translatable relative to each other in the "delivery" configuration.

Figure 3:
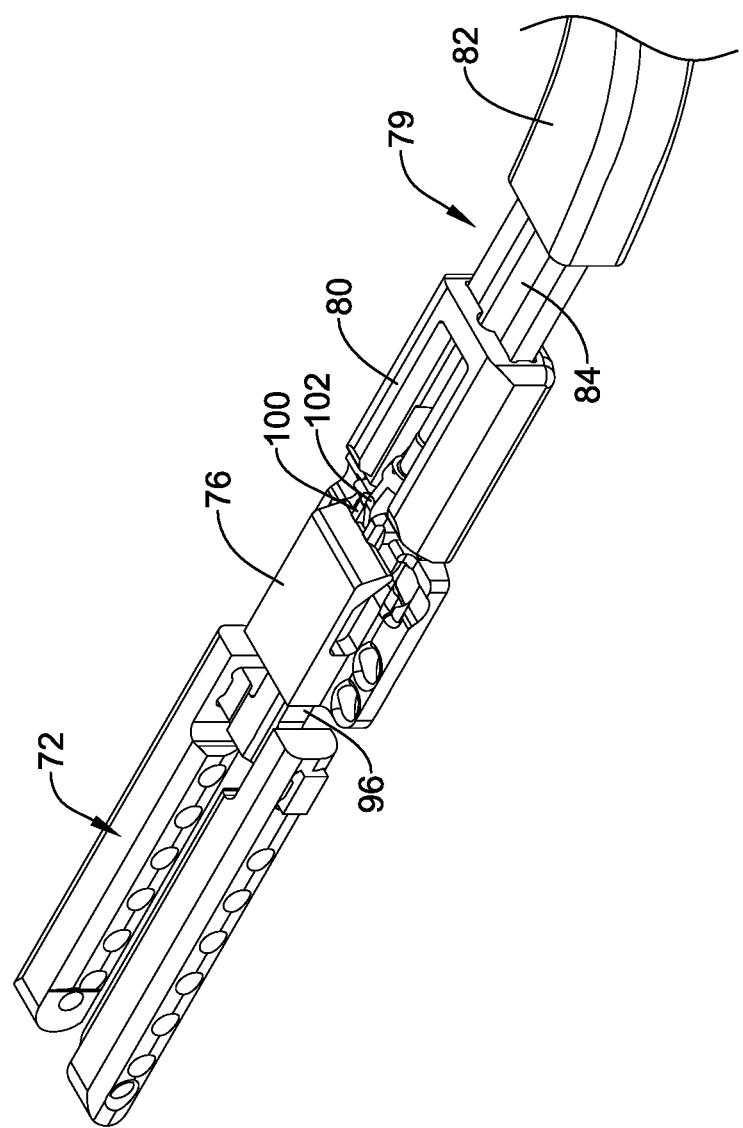
FIG. 3 illustrates selected components of an example implant associated with an example medical device system in a deployed configuration.
Figure 4:
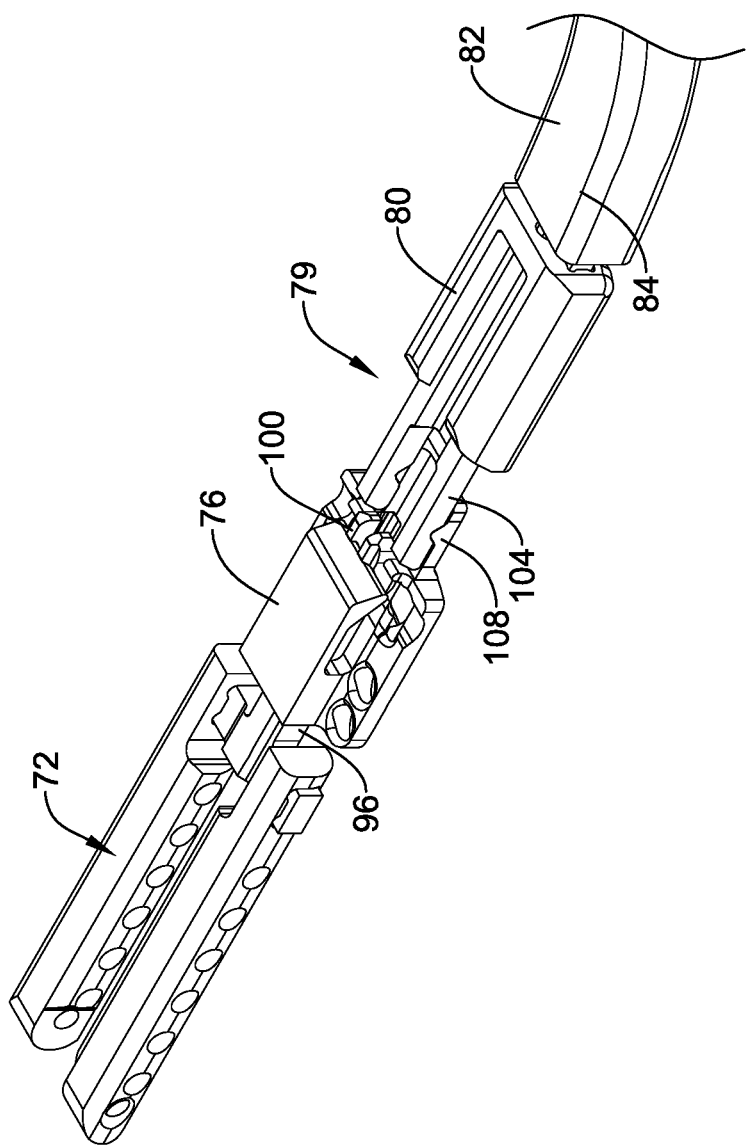
FIG. 4 illustrates selected components of an example implant associated with an example medical device system in a delivery configuration.
Figure 5:
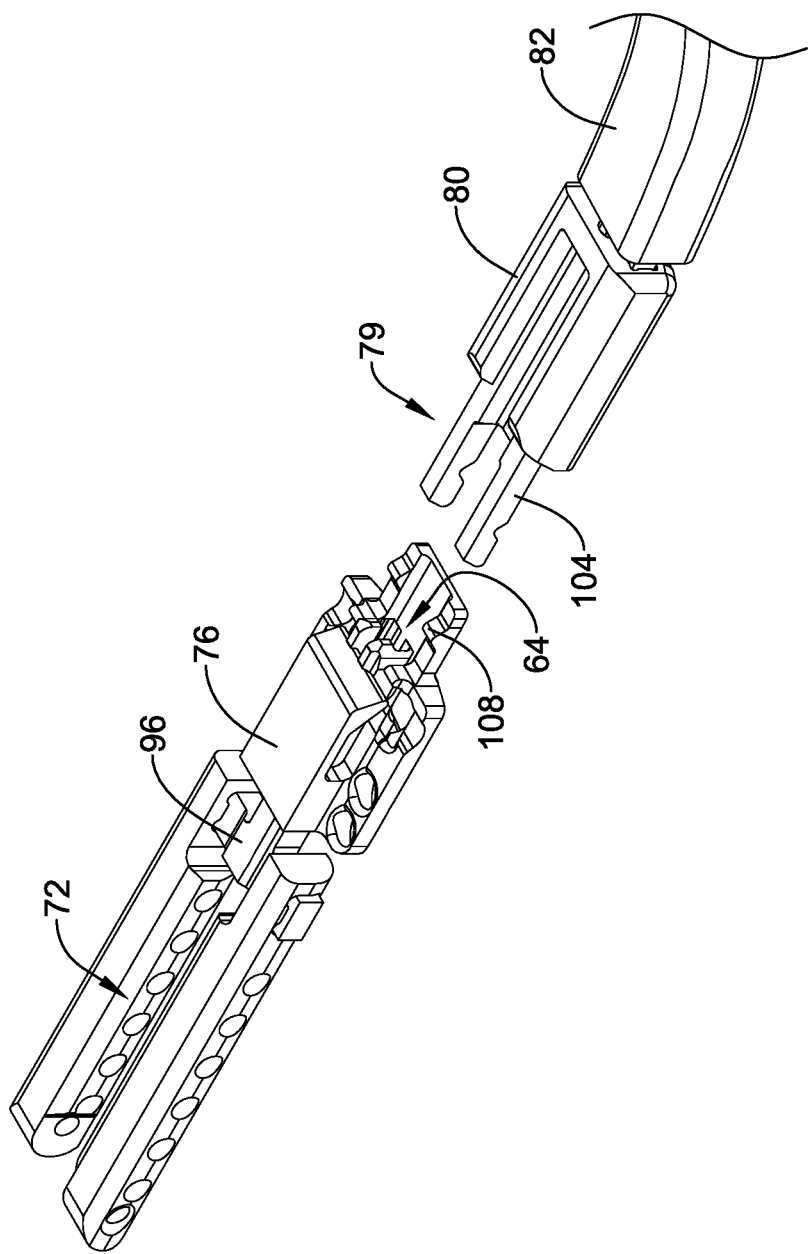
FIG. 5 illustrates selected components of an example implant associated with an example medical device system in a released configuration.
Figure 6:
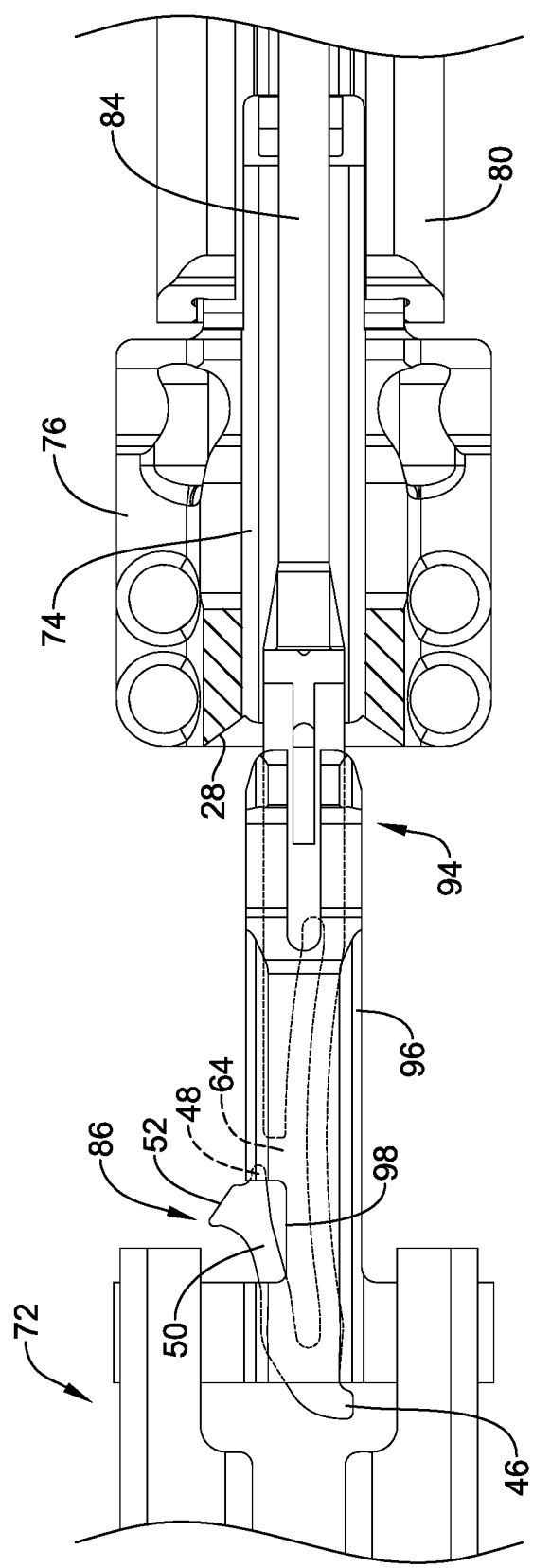
FIGS. 6-8 are a partial cross-sectional view of selected components of an example implant associated with an example medical device system.
Figure 7:
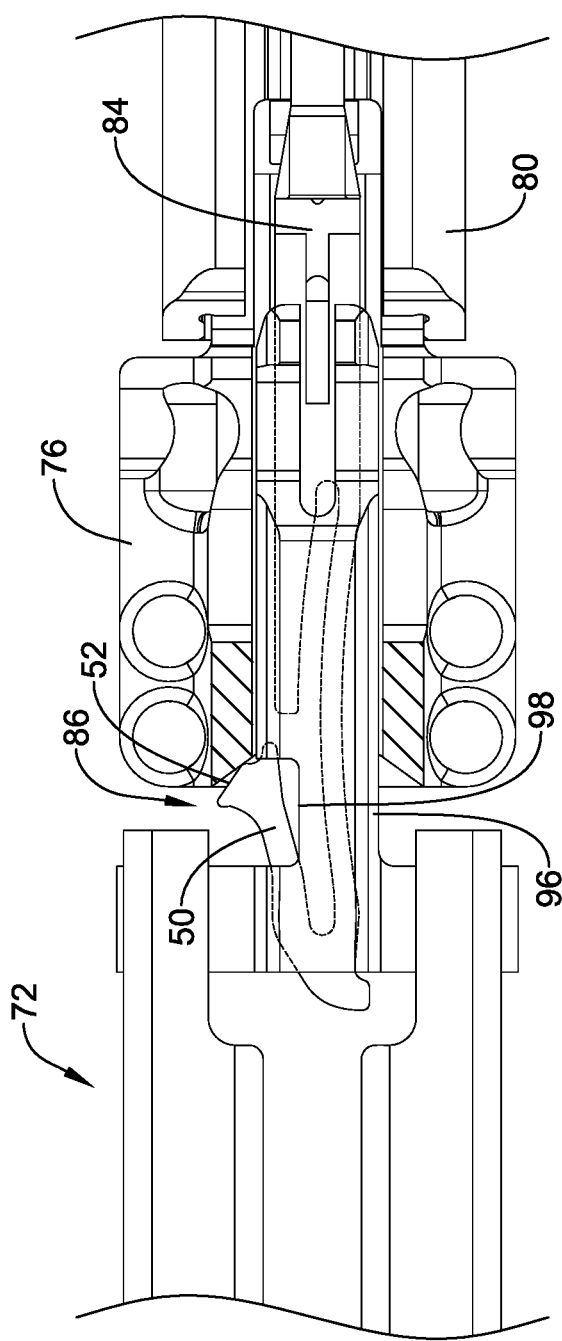
Figure 8:
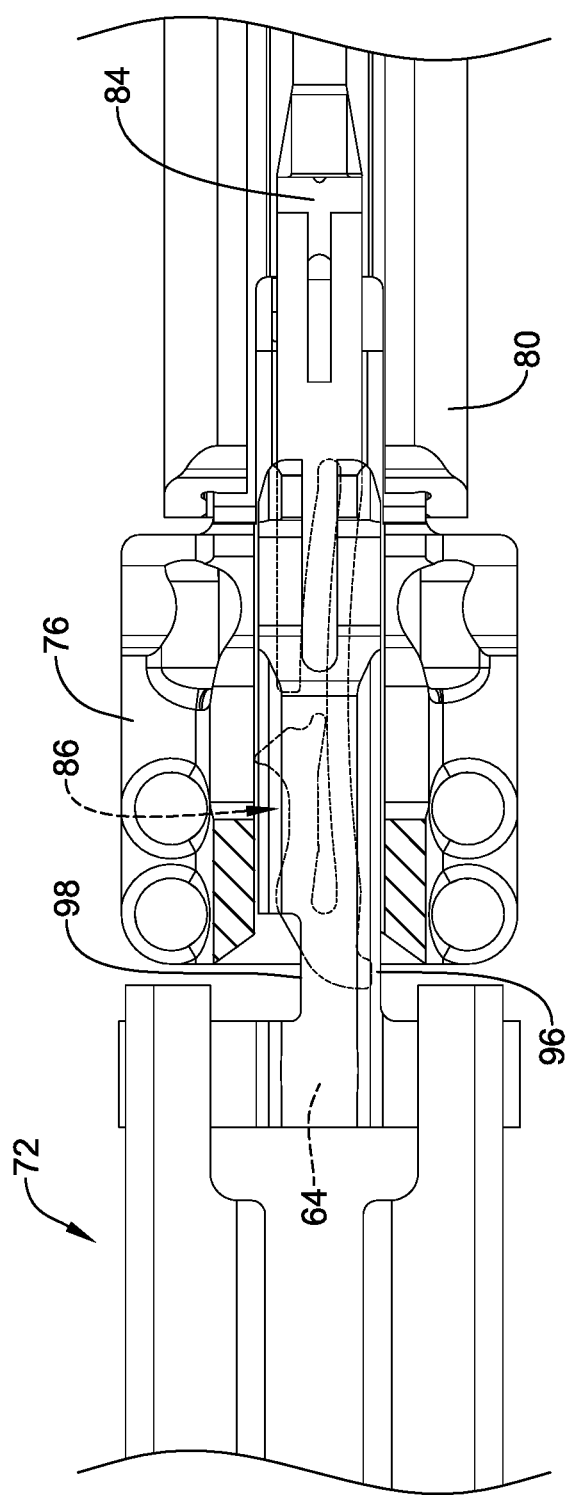
Figure 9:
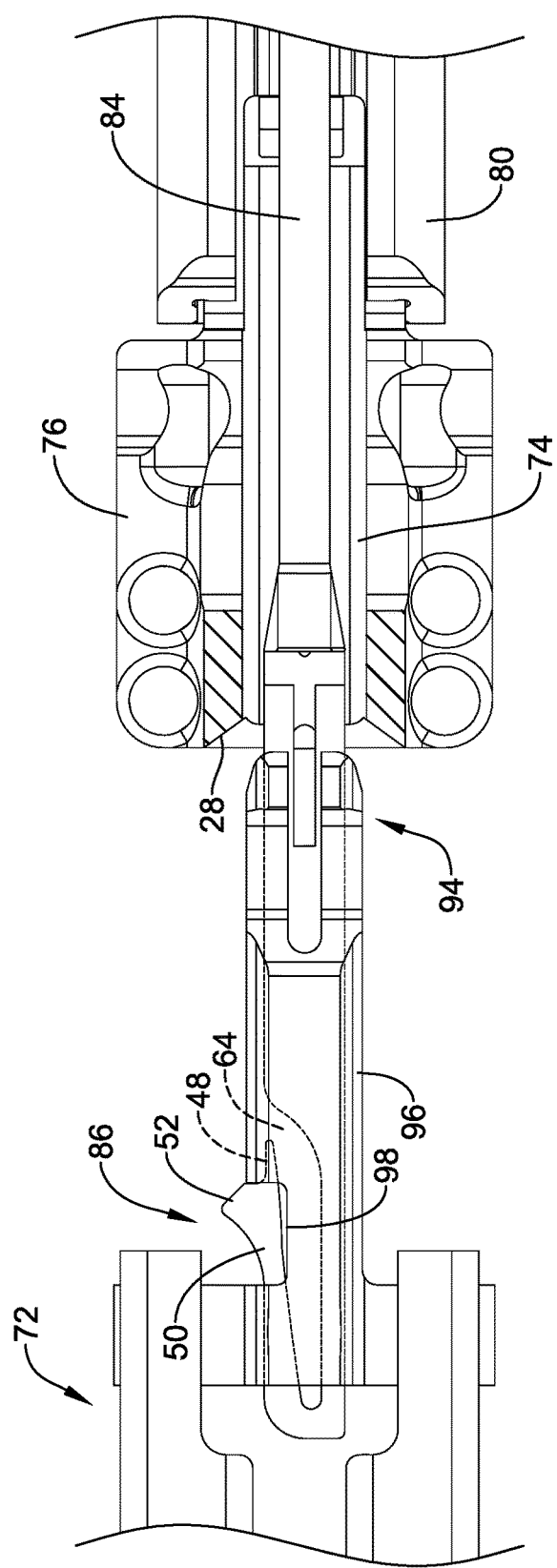
FIGS. 9-11 are a partial cross-sectional view of selected components of an example implant associated with an example medical device system.
Figure 10:
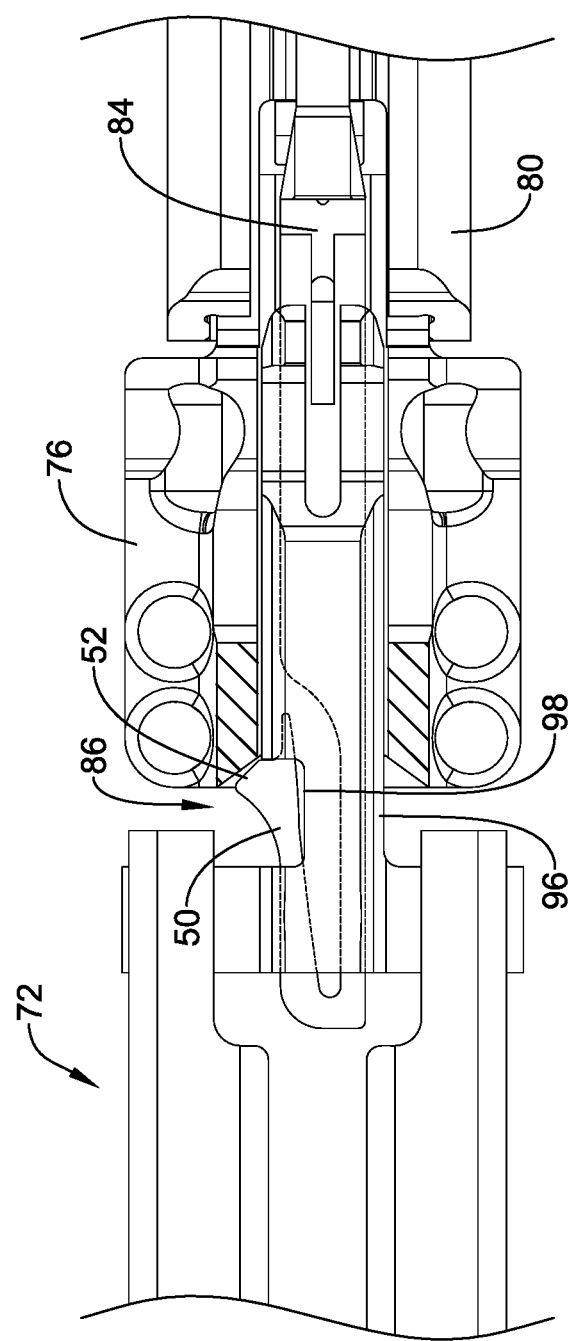
Figure 11:
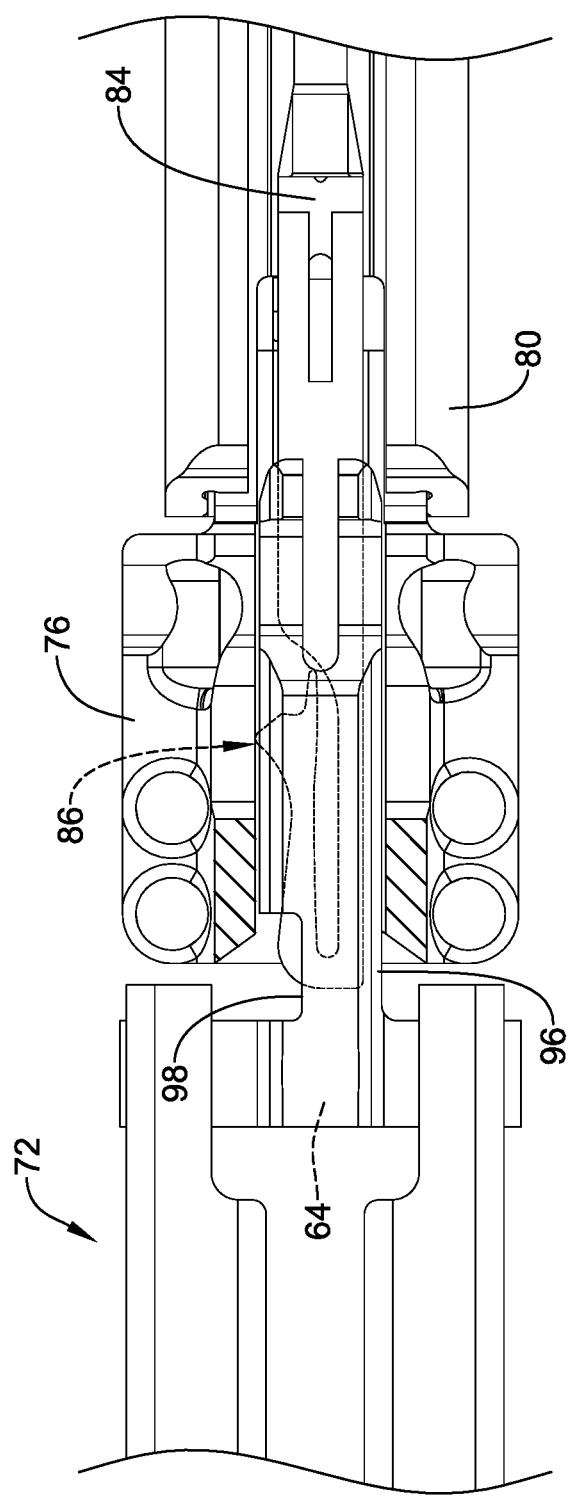

When medical implant 16 reaches the intended target site within the anatomy, a clinician can proximally retract the actuator element 84, thereby moving and/or translating the proximal end of the first locking portion 96 toward the distal end of the second locking portion 76 in order to axially shorten and/or radially expand the anchor member or braid 70 of the medical implant 16 towards the "deployed" configuration. When retracting or pulling the actuator element 84 proximally, the cam mechanism 86 extends through the at least one side aperture 98 in the first locking portion 96. Ultimately, the actuator element 84 can be retracted sufficiently far enough to engage the first transversely-oriented ridge 100 of the first locking portion 96 with a flap portion (described in more detail below) of the second locking portion 76 so as to lock the medical implant 16 and/or the anchor member or braid 70 in the "deployed" configuration (as seen in FIGS. 3-5, for example), suitable for implantation within the anatomy. In other words, in some embodiments, axial translation of the actuator element 84 in a first (e.g., proximal) direction may actuate the anchor member or braid 70 from the "delivery" configuration to the "deployed" configuration.

In some embodiments and/or some procedures, it may be desirable to unlock the anchor member or braid 70 from the "deployed" configuration and extend the anchor member or braid 70 back toward the "delivery" configuration in order to reposition or retract/remove the medical implant 16, for example. To do so, a clinician may urge and/or translate the actuator element 84 in a second (e.g., distal) direction to "unlock" the anchor member or braid 70. Axial translation of the actuator element 84 in the second (e.g., distal) direction relative to the at least one locking element 58 (i.e., the first locking portion 96 and/or the second locking portion 76) may slidably engage the unlocking member 102 with the second locking portion 76, thereby translating the flap portion of the second locking portion 76 away from a central longitudinal axis of the actuator element 84 and permitting the first transversely-oriented ridge 100 to pass back through the second locking portion 76.

Alternatively, if a clinician is satisfied with the positioning and/or locking of the medical implant 16 (e.g., after visualization of the medical implant 16 via a suitable imaging technique), the actuator element 84 may be uncoupled from the first locking portion 96, as shown in FIG. 4. Once the anchor member or braid 70 is locked into the "deployed" configuration, further axial translation of the actuator element 84 in the first (e.g., proximal) direction may deflect the cam mechanism 86, thereby disengaging and/or detaching the actuator element 84 from the first locking portion 96, which thereafter permits the actuator element 84 to be withdrawn from the first locking portion 96.

Once the actuator element 84 has been disengaged and/or detached from the first locking portion 96, further retraction of the actuator element 84 may cause the unlocking member 102 to engage a distal end of the collar 80 and slide the collar 80 proximally along the finger 79 while withdrawing the actuator element 84 from within the first locking portion 96 and/or the second locking portion 76. In doing so, the two elongated tines 104 of the finger 79 may be exposed and uncoupled from the rail 108, as seen in FIG. 5, which are configured to mate with the two elongated tines 104, as shown in FIG. 4. Thereafter, the medical device system 10 may be removed from the anatomy, leaving behind the expanded and deployed medical implant 16 disposed at the target site in a "released" configuration.

Figure 21:
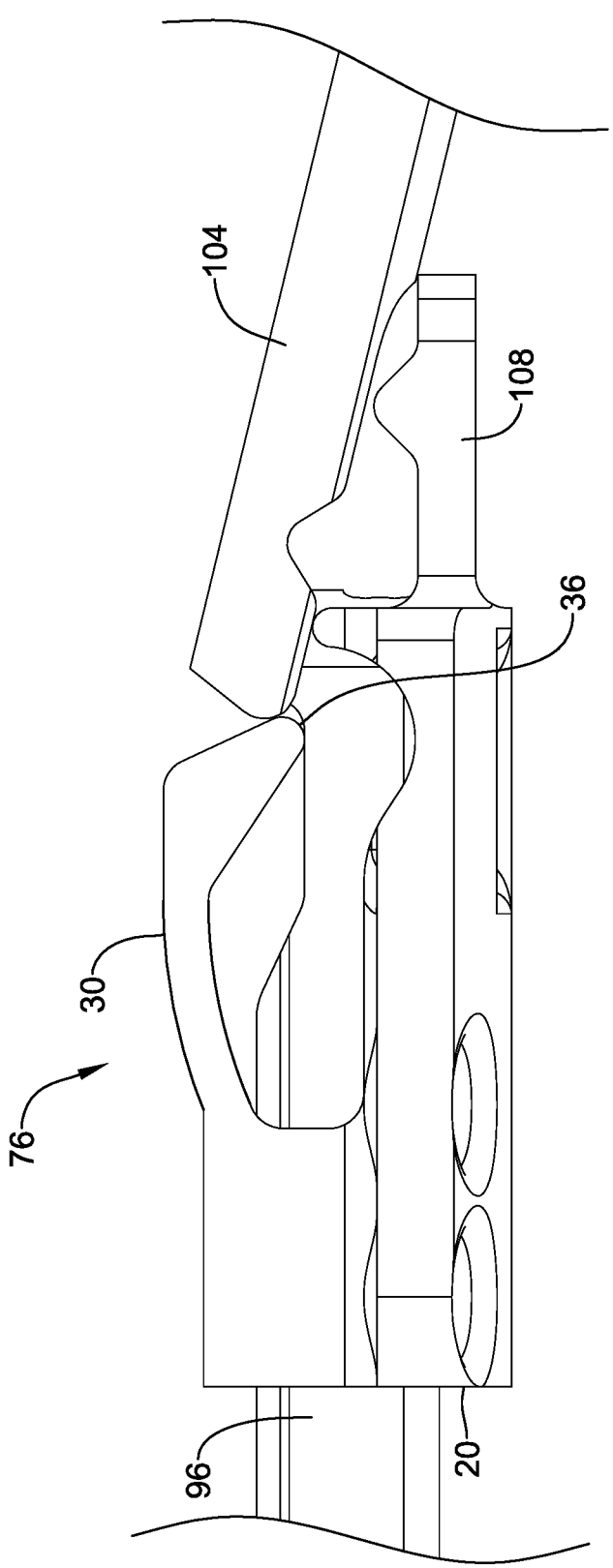
FIG. 21 is a partial side view of selected components of an example implant associated with an example medical device system.

In some embodiments, the second locking portion 76 may include a base portion 20 having a longitudinal axis extending between a proximal end and a distal end thereof, the base portion defining a top surface 22 and a bottom surface 24, as seen in FIG. 21 for example. In some embodiments, the second locking portion 76 may include a body portion 26 defining a longitudinal channel 74 extending therethrough. In at least some embodiments, the longitudinal channel 74 may be oriented substantially parallel to the longitudinal axis of the base portion 20. In some embodiments, at least a part of the body portion 26 may extend upwardly from a distal portion of the top surface 22 of the base portion 20.

In some embodiments, the second locking portion 76 may include a flap portion 30 extending proximally and/or toward the proximal end of the base portion 20 from the body portion 26. In some embodiments, the flap portion 30 may include a second transversely-oriented ridge 36 extending downwardly toward the base portion 20 and laterally across the base portion 20, such that when the second locking portion 76 is viewed along the longitudinal axis of the base portion 20, the second transversely-oriented ridge 36 obstructs at least a portion of the longitudinal channel 74.

In some embodiments, the base portion 20 may include a plurality of protrusions 32 extending upwardly from the top surface 22 and/or the base portion 20 at a location proximal of the flap portion 30. In some embodiments, the plurality of protrusions 32 may extend upwardly to a height above the top surface 22 greater than a proximalmost edge of the flap portion 30. In some embodiments, the plurality of protrusions 32 may extend laterally to a distance from the longitudinal axis of the base portion 20 equal to or greater than the flap portion 30. In at least some embodiments, the second locking portion 76 may be configured to slidably receive at least a portion of the elongated member of the first locking portion 96 within the longitudinal channel 74, as seen in FIG. 22 for example. In some embodiments, the second locking portion 76 may include one or more holes or other features provided to aid in attaching the second locking portion 76 to the anchor member or braid 70.

In some embodiments, the body portion 26 of the second locking portion 76 may include at least one ramp 28 tapering into the longitudinal channel 74 at a distal end thereof. In some embodiments, the at least one ramp 28 may be configured to engage and/or urge the cam mechanism 86 extending through the at least one side aperture 98 inwardly, thereby releasing the at least one actuator element 84 from the first locking portion 96.

In some embodiments, the cam mechanism 86 may include a first leg 50 extending from a distal portion of the actuator element 84. In some embodiments, the first leg 50 may form a generally U-shaped member extending distally from the distal portion of the actuator element 84 and then turning and continuing back proximally toward the distal portion of the actuator element 84 to a transversely extending first projection 52 being configured to engage the first locking portion 96 and/or extend through the at least one side aperture 98, as seen in FIGS. 6-11 for example. In some embodiments, the cam mechanism 86 and/or the first leg 50 may be self-biased to spread, expand, and/or bend laterally outward away from and/or relative to a central longitudinal axis of the actuator element 84.

In some embodiments, the first leg 50 may include a spear 48 extending proximally from the first projection 52. In some embodiments, the spear 48 may be configured to rest against an inner surface of the passageway 64 when the first projection 52 extends through the at least one side aperture 98. In some embodiments, the cam mechanism 86 may include a lateral bumper member 46 disposed at a distalmost end thereof. In some embodiments, the bumper member 46 may be configured to engage and/or abut a distal end surface of the first locking portion 96 when the first projection 52 extends through the at least one side aperture 98.

Figure 12:
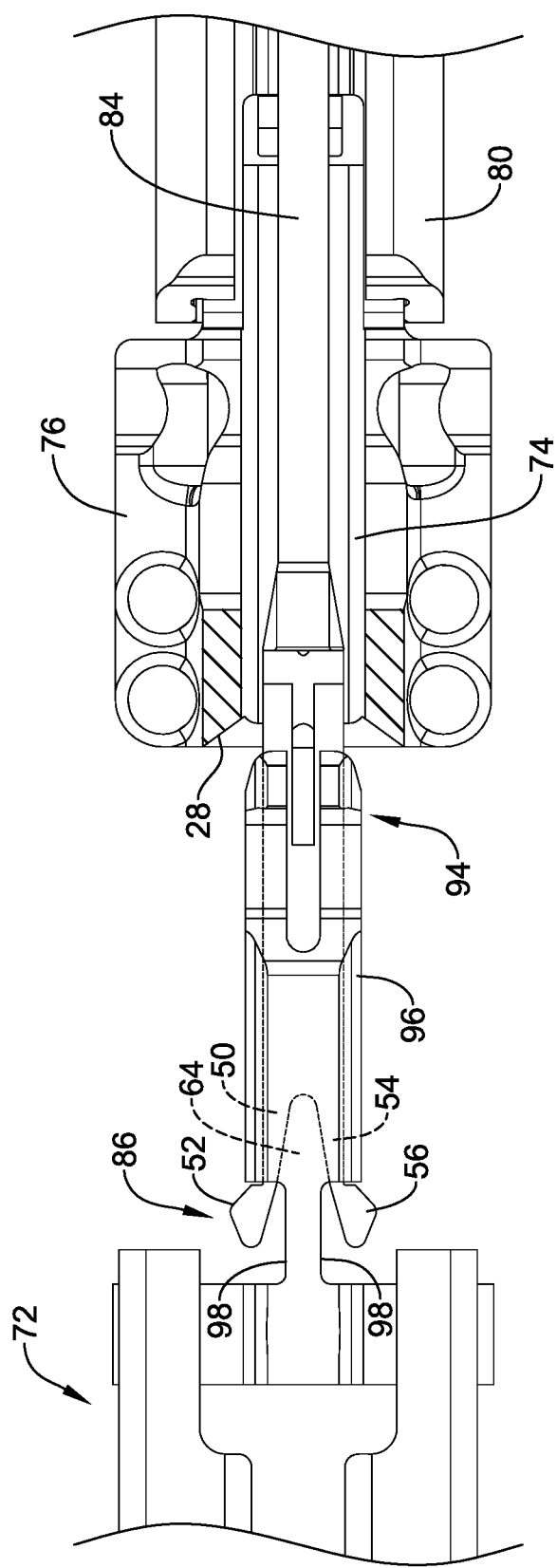
FIGS. 12-14 are a partial cross-sectional view of selected components of an example implant associated with an example medical device system.
Figure 13:
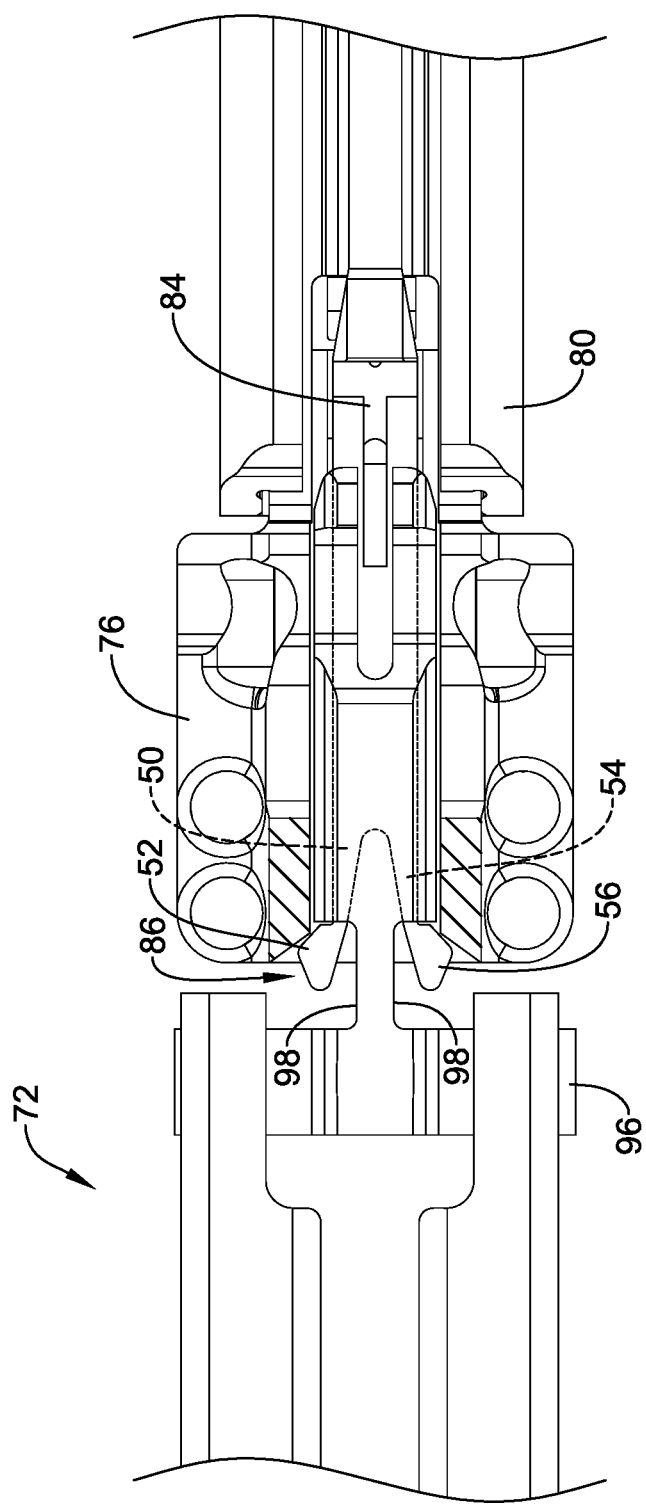
Figure 14:
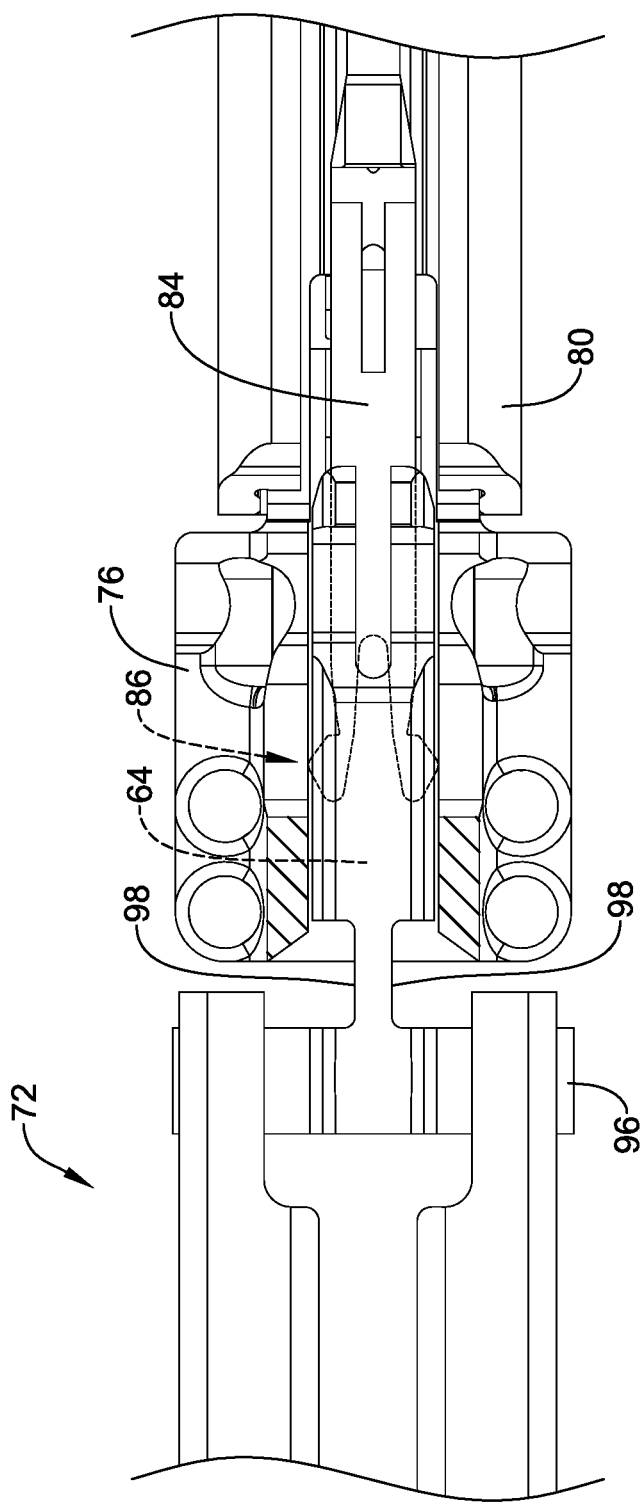

In some embodiments, the first leg 50 may extend distally from the distal portion of the actuator element 84 and outwardly from a central longitudinal axis of the actuator element 84 to a transversely extending first projection 52 configured to engage the first locking portion 96 and/or extend through the at least one side aperture 98, as seen in FIGS. 12-14 for example.

Figure 15:
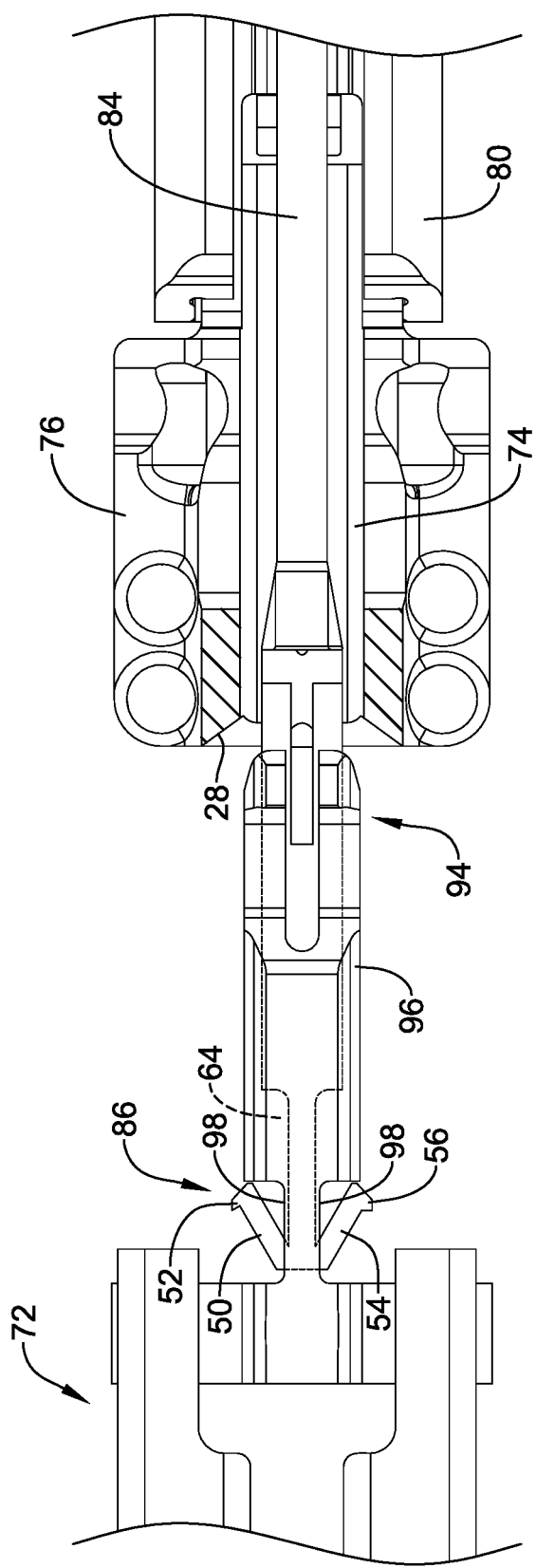
FIGS. 15-17 are a partial cross-sectional view of selected components of an example implant associated with an example medical device system.
Figure 16:
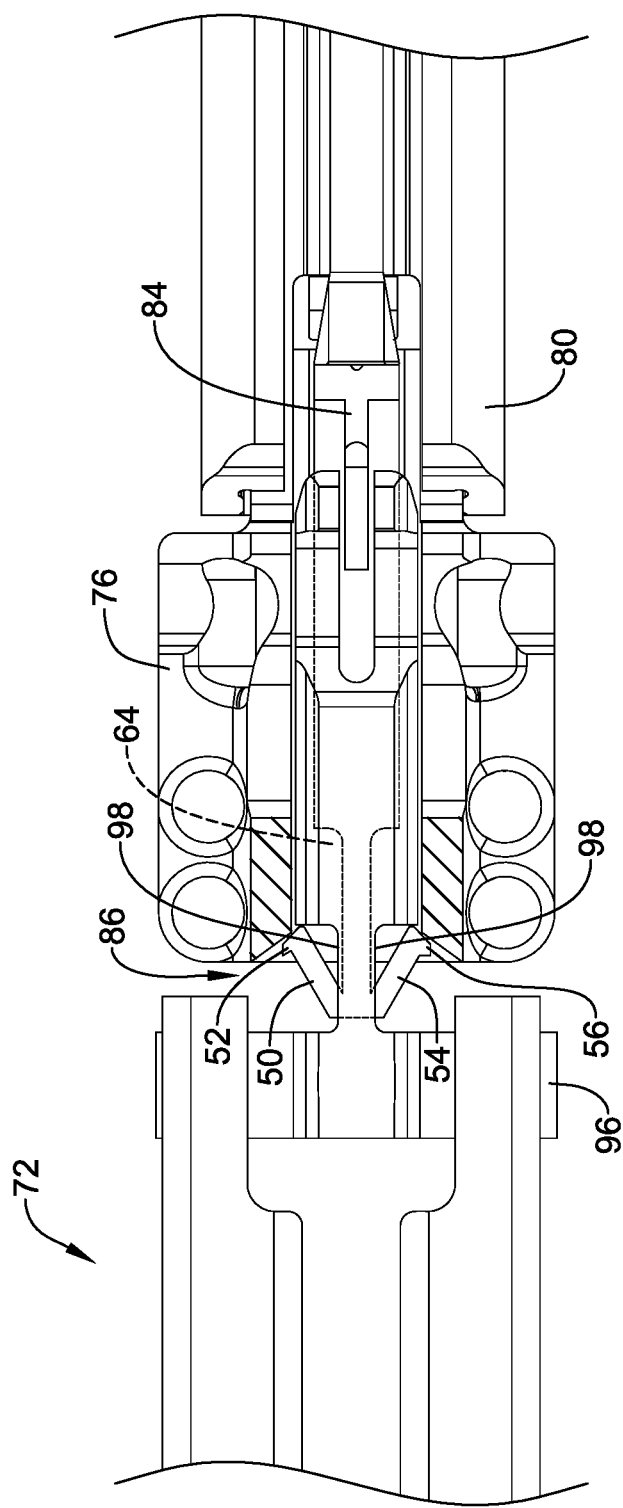
Figure 17:
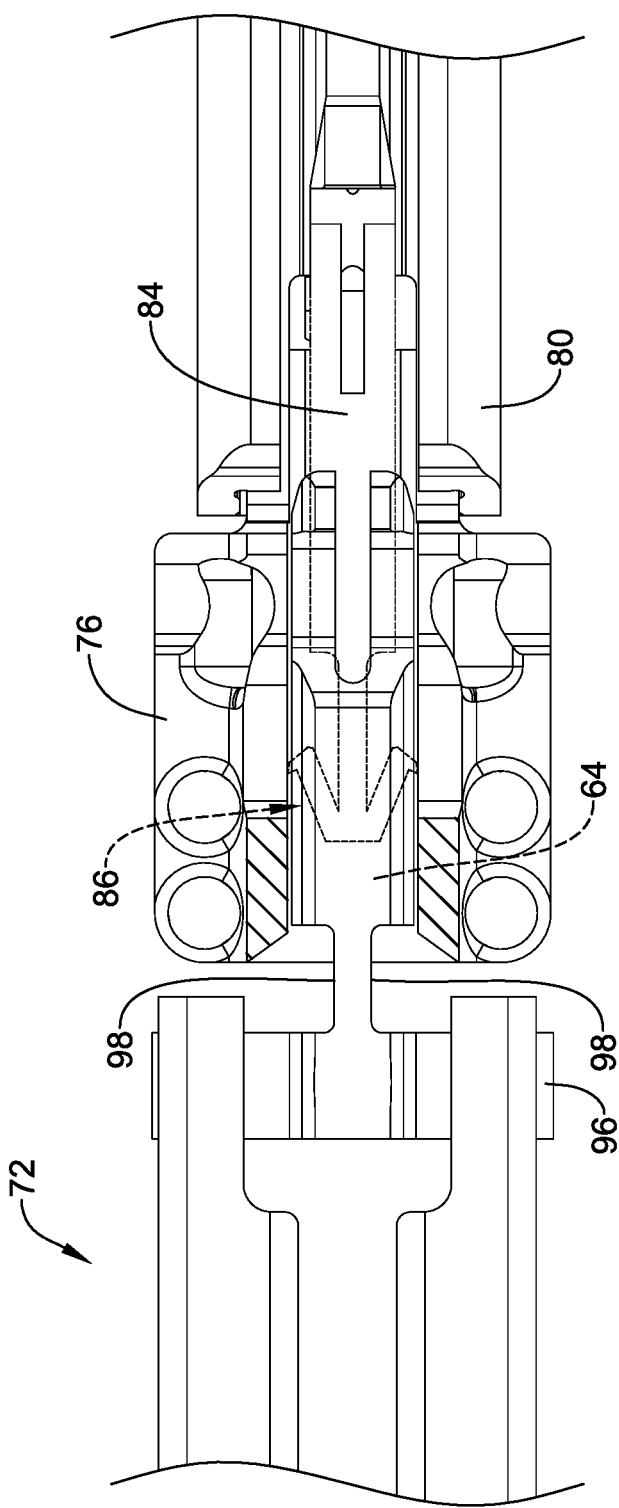

In some embodiments, the first leg 50 may extend proximally from the distal portion of the actuator element 84 and outwardly from a central longitudinal axis of the actuator element 84 to a transversely extending first projection 52 configured to engage the first locking portion 96 and/or extend through the at least one side aperture 98, as seen in FIGS. 15-17 for example.

In some embodiments, the cam mechanism 86 may include a second leg 54 extending from a distal portion of the actuator element 84. In some embodiments, the second leg 54 may form a generally U-shaped member extending distally from the distal portion of the actuator element 84 and then continuing back proximally toward the distal portion of the actuator element 84 to a transversely extending second projection 56 configured to engage the first locking portion 96 and/or extend through the at least one side aperture 98. In some embodiments, the second leg 54 may extend distally from the distal portion of the actuator element 84 and outwardly from a central longitudinal axis of the actuator element 84 to a transversely extending second projection 56 configured to engage the first locking portion 96 and/or extend through the at least one side aperture 98, as seen in FIGS. 12-14 for example. In some embodiments, the cam mechanism 86 and/or the second leg 54 may be self-biased to spread, expand, and/or bend laterally outward away from and/or relative to a central longitudinal axis of the actuator element 84.

In some embodiments, the second leg 54 may extend proximally from the distal portion of the actuator element 84 and outwardly from a central longitudinal axis of the actuator element 84 to a transversely extending second projection 56 configured to engage the first locking portion 96 and/or extend through the at least one side aperture 98, as seen in FIGS. 15-17 for example. In some embodiments having a first leg 50, a second leg 54, and two side apertures 98, the first projection 52 may extend through a first side aperture and the second projection 56 may extend through a second side aperture opposite the first side aperture.

In some embodiments, the actuator element 84 may be disposed within and/or extend axially and/or longitudinally through the longitudinal channel 74 of the second locking portion 76 and may be releasably coupled to the first locking portion 96. In at least some embodiments, the actuator element 84 may be axially translatable through the body portion 26 of the second locking portion 76.

Figure 18:
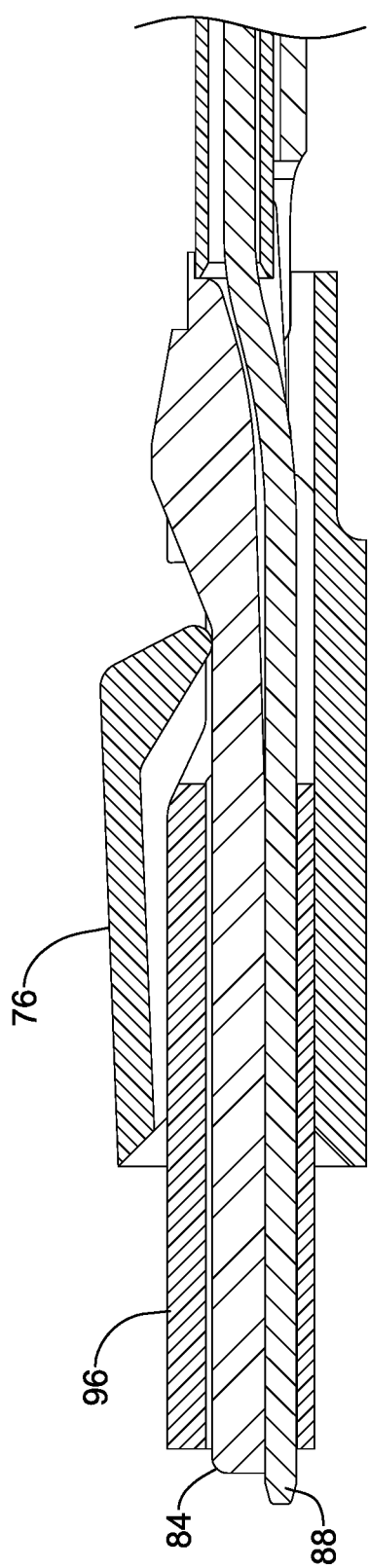
FIG. 18 is a partial cross-sectional view of selected components of an example implant associated with an example medical device system.
Figure 19:
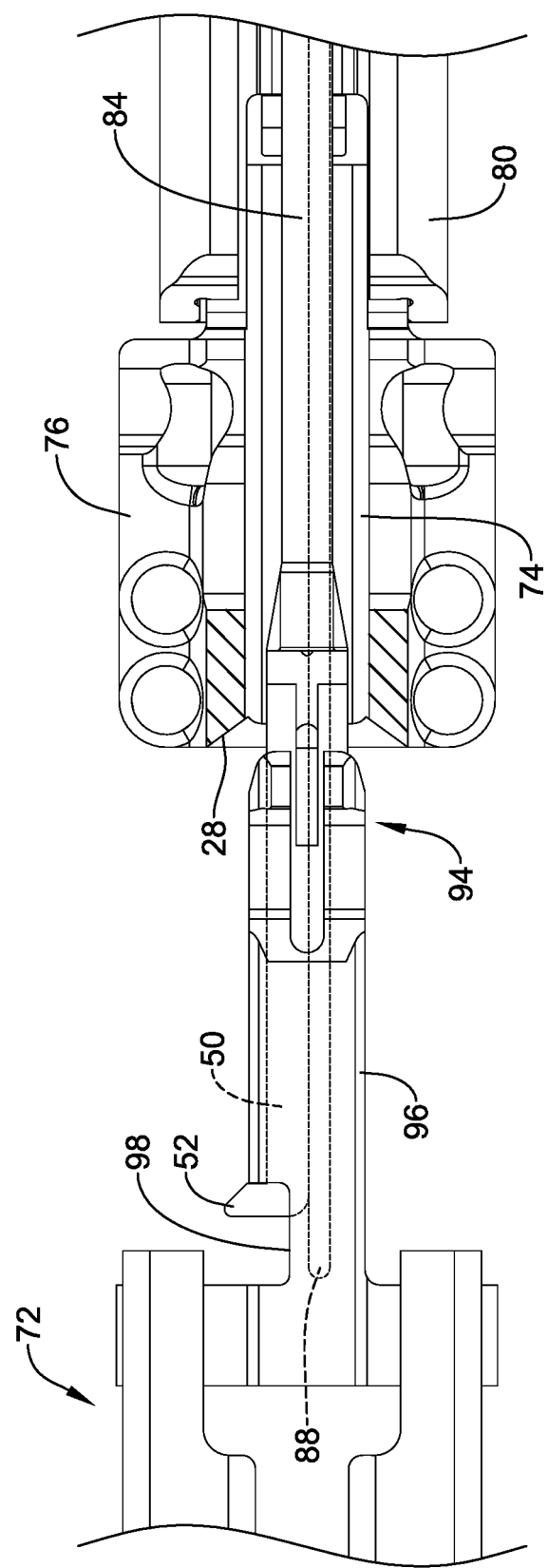
FIG. 19 is a partial cross-sectional view of selected components of an example implant associated with an example medical device system.

In some embodiments, the at least one actuator element 84 may include a retractable release pin 88, as seen in FIGS. 18-19 for example. In some embodiments, the retractable release pin 88 may be slidably disposed within a bore of the at least one actuator element 84. In some embodiments, a distal portion of the retractable release pin 88 may be disposed alongside the self-biased cam mechanism 86. In some embodiments, the retractable release pin 88 may engage with the first locking portion 96 such that the at least one actuator element 84 is prevented from disengaging the first locking portion 96. In some embodiments, a distal portion of the retractable release pin 88 may be disposed within the longitudinally-extending passageway 64 of the first locking portion 96 alongside the first leg 50. In some embodiments, a distal portion of the retractable release pin 88 may be disposed within the longitudinally-extending passageway 64 of the first locking portion 96 alongside the first leg 50, thereby preventing the cam mechanism 86 from disengaging the first locking portion 96. In some embodiments, a distal portion of the retractable release pin 88 may be disposed within the longitudinally-extending passageway 64 of the first locking portion 96 alongside the first leg 50, thereby preventing the first projection 52 from disengaging the at least one side aperture 98 of the first locking portion 96. Use may be similar to that described below, and after locking the anchor member or braid 70 in the "deployed" configuration, the release pin 88 may be withdrawn proximally, thereby permitting the at least one actuator element 84 to disengage and/or detach from the first locking portion 96 in the absence of the release pin 88 within the passageway 64.

Figure 20:
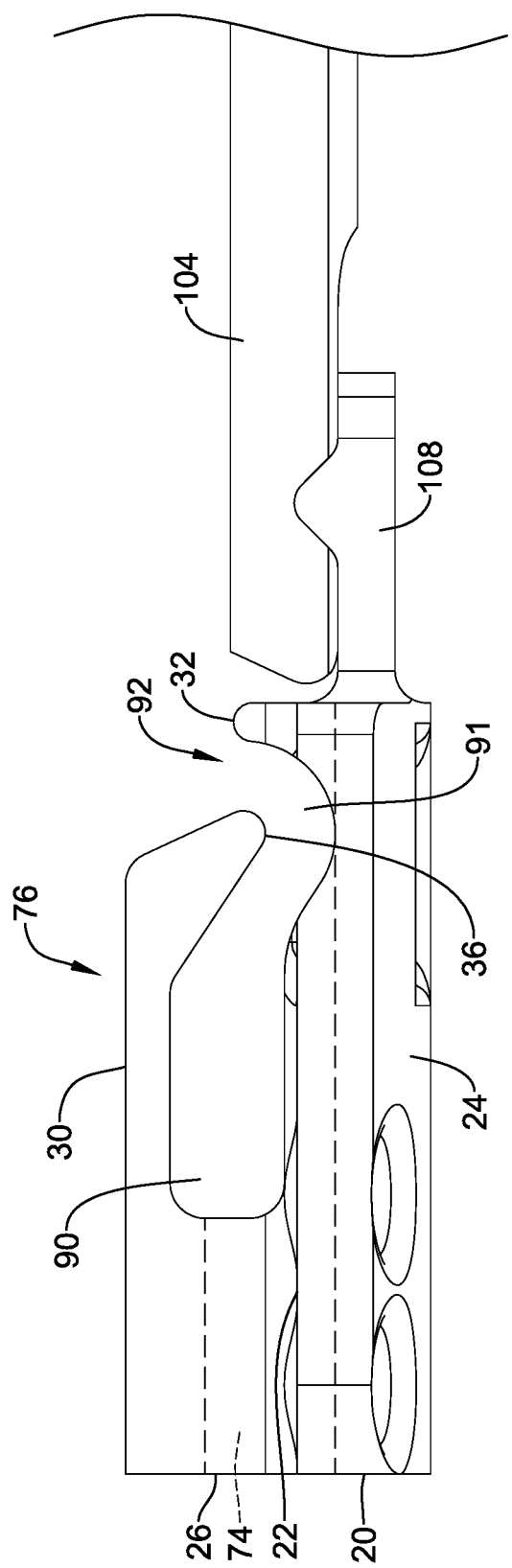
FIG. 20 is a partial side view of selected components of an example implant associated with an example medical device system.

In some embodiments, a profile of the second locking portion 76 (i.e., as viewed laterally or from the side relative to the longitudinal axis of the base portion 20, as seen in FIG. 20 for example) may include a generally rectangular pocket 90 disposed between the flap portion 30 and the top surface 22, and a passage 91 extending proximally from the generally rectangular pocket 90 in a curve extending toward the bottom surface 24 around a proximalmost tip of the flap portion 30 (and/or the second transversely-oriented ridge 36) and then back away from the bottom surface 24 between the proximalmost tip of the flap portion 30 (and/or the second transversely-oriented ridge 36) and the plurality of protrusions 32 to an upwardly-facing opening 92. In some embodiments, the plurality of protrusions 32 may define an upwardmost edge disposed at a greater distance from the bottom surface 24 than a bottommost edge of the flap portion 30 (and/or the second transversely-oriented ridge 36).

In use, a distal portion of the at least one actuator element 84, which may include a cam mechanism 86, may be slidably received within a passageway 64 of the first locking portion 96. At least a portion of the cam mechanism 86, which may include a first projection 52 may engage and/or extend through the at least one side aperture 98 of the first locking portion 96. In at least some embodiments, the first projection 52 may include a proximal face angled toward a central longitudinal axis of the at least one actuator element 84 and/or the base portion 20 in the first (e.g., proximal) direction. Proximal withdrawal and/or translation of the at least one actuator element 84 may draw a proximal end of the first locking portion 96 proximally toward a distal end of the second locking portion 76 and into the longitudinal channel 74 of the second locking portion 76. As the first locking portion 96 is translated proximally relative to the second locking portion 76, the first transversely-oriented ridge 100 of the first locking portion 96 engages the second transversely-oriented ridge 36 of the second locking portion 76 to lock the anchor member or braid 70 into the "deployed" configuration. At or about the same time and/or position, the first projection 52 and/or the proximal face thereof may come into contact and/or engagement with the at least one ramp 28 of the second locking portion 76. Continued proximal retraction and/or translation of the at least one actuator element 84 may result in a noticeable and/or substantial increase in force required to withdraw and/or translate the at least one actuator element 84 in the first (e.g., proximal) direction. The increase in force may provide tactile feedback to the operator/practitioner indicating that the anchor member or braid 70 has been locked in the "deployed" configuration. Following locking of the anchor member or braid 70 in the "deployed" configuration and engagement of the first projection 52 and/or the proximal face thereof with the at least one ramp 28, further proximal withdrawal and/or translation of the at least one actuator element 84 relative to the at least one locking element 58 may urge the cam mechanism 86 to bend and/or deflect inward toward the central longitudinal axis of the at least one actuator element 84 and/or into the longitudinal channel 74, thereby permitting the cam mechanism 86 and/or the first leg 50 to disengage from the first locking portion 96 and translate proximally within the passageway 64 thereof. Withdrawal of the at least one actuator element 84 completely from the first locking portion 96 releases the anchor member or braid 70 from the at least one actuator element 84 and leaves the medical implant 16 disposed at the target site in the "released" configuration. Disengagement of the at least one actuator element 84 and release of the anchor member or braid 70 and/or the medical implant 16 may be controlled by distance travelled by the at least one actuator element 84 relative to the second locking portion 76.

In some embodiments having a second leg 54 and/or a second projection 56, the operation may be substantially similar. In at least some embodiments, the second projection 56 may include a proximal face angled toward a central longitudinal axis of the at least one actuator element 84 and/or the base portion 20 in the first (e.g., proximal) direction. As the first locking portion 96 is translated proximally relative to the second locking portion 76, the first transversely-oriented ridge 100 of the first locking portion 96 engages the second transversely-oriented ridge 36 of the second locking portion 76 to lock the anchor member or braid 70 into the "deployed" configuration. At or about the same time and/or position, the first projection 52, the second projection 56, and/or the proximal faces thereof may come into contact and/or engagement with the at least one ramp 28 of the second locking portion 76. Continued proximal retraction and/or translation of the at least one actuator element 84 may result in a noticeable and/or substantial increase in force required to withdraw and/or translate the at least one actuator element 84 in the first (e.g., proximal) direction. The increase in force may provide tactile feedback to the operator/practitioner indicating that the anchor member or braid 70 has been locked in the "deployed" configuration. Following locking of the anchor member or braid 70 in the "deployed" configuration and engagement of the first projection 52, the second projection 56, and/or the proximal faces thereof with the at least one ramp 28, further proximal withdrawal and/or translation of the at least one actuator element 84 relative to the at least one locking element 58 may urge the cam mechanism 86 to bend and/or deflect inward toward the central longitudinal axis of the at least one actuator element 84 and/or into the longitudinal channel 74, thereby permitting the cam mechanism 86 and/or the first leg 50 and the second leg 54 to disengage from the first locking portion 96 and translate proximally within the passageway 64 thereof. Withdrawal of the at least one actuator element 84 completely from the first locking portion 96 releases the anchor member or braid 70 from the at least one actuator element 84 and leaves the medical implant 16 disposed at the target site in the "released" configuration.

In some embodiments, a method of releasing a valve replacement implant from a delivery device, wherein the implant includes an anchor member or braid 70 reversibly actuatable between a delivery configuration and a deployed configuration and at least one locking element 58 configured to lock the anchor member or braid 70 in the deployed configuration, and the delivery device includes at least one actuator element 84 configured to engage the at least one locking element 58 and actuate the anchor member or braid 70 between the delivery configuration and the deployed configuration, wherein the at least one actuator element 84 includes a self-biased cam mechanism 86 configured to extend into and engage a first locking portion 96 of the at least one locking element 58, may include guiding the implant to a target location in the delivery configuration with the delivery device, retracting the at least one actuator element 84 such that a first transversely-oriented ridge 100 on the first locking portion 96 engages a second transversely-oriented ridge 36 on a second locking portion 76, thereby locking the anchor member in the deployed configuration, receiving tactile feedback that the anchor member or braid 70 has achieved the deployed configuration, further retracting the at least one actuator element 84 to disengage the at least one actuator element 84 from the first locking portion 96, and withdrawing the at least one actuator element 84 from the at least one locking element 58, thereby leaving the implant at the target location. In some embodiments, the tactile feedback may include an increase in force required to retract the at least one actuator element 84. In some embodiments, a method of releasing a valve replacement implant may include, after receiving tactile feedback, verifying positioning of the implant within the target location, advancing the at least one actuator element 84 distally to unlock the anchor member or braid 70 from the deployed configuration, repositioning the implant at the target location, and retracting the at least one actuator element 84 to re-lock the anchor member or braid 70 in the deployed configuration.

In at least some embodiments, the actuator element 84 may be formed from a solid wire or rod. In some embodiments, at least a portion of the solid wire or rod may be machined, ground, or otherwise had material removed or added to form a stepped structure. In some embodiments, the actuator element 84 may be tapered instead of stepped. Various combinations of these configurations are also contemplated. In at least some embodiments, the actuator element 84 may be releasably engaged to the first locking portion 96.

The materials that can be used for the various components of the medical device system 10 (and/or other systems disclosed herein) and the various tubular members disclosed herein may include those commonly associated with medical devices. For simplicity purposes, the following discussion makes reference to the outer sheath and/or the inner catheter. However, this is not intended to limit the devices and methods described herein, as the discussion may be applied to other similar tubular members and/or components of tubular members or devices disclosed herein, such as, but not limited to, the actuator elements, the first locking portions, the second locking portions, and/or elements or components thereof.

In some embodiments, the outer sheath and/or the inner catheter may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the outer sheath and/or the inner catheter may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, the outer sheath and the inner catheter, or portions thereof, may be made of a material that does not substantially distort the image and create substantial artifacts (i.e., gaps in the image). Certain ferromagnetic materials, for example, may not be suitable because they may create artifacts in an MRI image. The outer sheath and the inner catheter, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an outer sheath and/or an inner catheter of the medical device system 10, may be formed from a suitable polymer or other material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical device system 10 (including, for example, the exterior surface of the outer sheath and the inner catheter) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the outer sheath and the inner catheter, or other portions of the medical device system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Other suitable coatings may also be used.

The coating and/or the outer sheath and/or inner catheter may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:
1. A medical device system, comprising:
a valve replacement implant including an anchor member reversibly actuatable between a delivery configuration and a deployed configuration;
wherein the implant includes at least one locking element configured to lock the anchor member in the deployed configuration; and
at least one actuator element configured to engage the at least one locking element and actuate the anchor member between the delivery configuration and the deployed configuration;
wherein the at least one actuator element includes a self-biased cam mechanism configured to extend into and engage a first locking portion of the at least one locking element,
wherein the first locking portion includes a longitudinally-oriented passageway extending therethrough, and at least one side aperture extending transversely through a side wall of the first locking portion to the longitudinally-oriented passageway, the at least one side aperture being configured to receive the self-biased cam mechanism therein such that the self-biased cam mechanism extends through the at least one side aperture,
wherein the first locking portion of the at least one locking element is fixedly attached to the anchor member and a second locking portion of the at least one locking element is fixedly attached to the anchor member, the first locking portion and the second locking portion being longitudinally movable relative to each other in the delivery configuration, wherein the second locking portion includes:
a base portion having a longitudinal axis extending between a proximal end and a distal end, the base portion defining a top surface and a bottom surface;
a body portion defining a longitudinal channel extending therethrough, at least a part of the body portion extending upwardly from the base portion; and
a flap portion extending toward the proximal end from the body portion;
wherein the base portion includes a plurality of protrusions extending upwardly from the top surface proximal of the flap portion;
wherein the second locking portion is configured to slidably receive the first locking portion within the longitudinal channel.

2. The medical device system of claim 1, wherein the first locking portion is fixedly attached to a distal portion of the anchor member and the second locking portion is fixedly attached to a proximal portion of the anchor member.

3. The medical device system of claim 1, wherein the body portion includes at least one ramp tapering into the longitudinal channel at the distal end thereof;
wherein the at least one ramp is configured to engage the self-biased cam mechanism and urge the self-biased cam mechanism extending through the at least one side aperture inwardly, thereby releasing the at least one actuator element from the first locking portion.

4. The medical device system of claim 1, wherein the flap portion includes a transversely-oriented ridge extending downwardly toward the base portion and laterally across the base portion, such that when the second locking portion is viewed along the longitudinal axis, the transversely-oriented ridge obstructs at least a portion of the longitudinal channel.

5. The medical device system of claim 1, wherein the plurality of protrusions extends upwardly to a height above the top surface greater than a proximalmost edge of the flap portion.

6. The medical device system of claim 1, wherein the plurality of protrusions extends laterally to a distance from the longitudinal axis equal to or greater than the flap portion.

7. The medical device system of claim 1, wherein the flap portion is self-biased toward an equilibrium position relative to the base portion.

8. The medical device system of claim 1, wherein the first locking portion includes an engagement portion having a first transversely-oriented ridge adjacent a proximal end thereof.

9. The medical device system of claim 8, wherein the flap portion engages the first transversely-oriented ridge in the deployed configuration.

10. The medical device system of claim 1, wherein the self-biased cam mechanism includes a first leg having a transversely extending first projection configured to engage the first locking portion.

11. The medical device system of claim 10, wherein the self-biased cam mechanism further includes a second leg having a transversely extending second projection, the second projection extending in a direction opposite the first projection.

12. The medical device system of claim 10, wherein the at least one actuator element includes a retractable release pin disposed alongside the first leg, thereby preventing the self-biased cam mechanism from disengaging the first locking portion.

13. The medical device system of claim 12, wherein the retractable release pin is slidably disposed within a bore of the at least one actuator element.

14. The medical device system of claim 1, wherein a profile of the second locking portion includes a generally rectangular pocket between the flap portion and the top surface; and a passage extending proximally from the generally rectangular pocket in a curve extending toward the bottom surface around a proximalmost tip of the flap portion and then back away from the bottom surface between the proximalmost tip of the flap portion and the plurality of protrusions to an upwardly-facing opening;
wherein the plurality of protrusions defines an upwardmost edge disposed at a greater distance from the bottom surface than a bottommost edge of the flap portion.

* * * * *